(12) United States Patent
Fiadeiro et al.

(10) Patent No.: US 12,018,290 B2
(45) Date of Patent: Jun. 25, 2024

(54) METHODS FOR CONTINUOUSLY INACTIVATING A VIRUS DURING MANUFACTURE OF A PROTEIN

(71) Applicant: Boehringer Ingelheim International GmbH, Ingelheim am Rhein (DE)

(72) Inventors: Marcus Andre Fiadeiro, Cambridge, MA (US); Jonathan Coffman, Union City, CA (US); Robert Lee Fahrner, Ellisville, MO (US); Jill Ann Kublbeck, Atkinson, NH (US); Raquel Orozco, El Cerrito, CA (US); Jeffrey Richard Salm, Wakefield, MA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/854,462

(22) Filed: Jun. 30, 2022

(65) Prior Publication Data
US 2022/0356454 A1    Nov. 10, 2022

Related U.S. Application Data

(62) Division of application No. 16/083,650, filed as application No. PCT/US2017/021714 on Mar. 10, 2017, now Pat. No. 11,407,981.

(60) Provisional application No. 62/307,287, filed on Mar. 11, 2016.

(51) Int. Cl.
*C12N 7/00* (2006.01)
*C07K 16/00* (2006.01)

(52) U.S. Cl.
CPC .............. *C12N 7/00* (2013.01); *C07K 16/00* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 5,429,746 | A | 7/1995 | Shadle et al. |
| 6,875,848 | B2 | 4/2005 | Ristol Debart et al. |
| 7,993,580 | B2 | 8/2011 | Anderle et al. |
| 10,435,670 | B2 * | 10/2019 | Coffman ................. C12N 7/00 |
| 11,407,981 | B2 | 8/2022 | Fiadeiro et al. |
| 2013/0236358 | A1 | 9/2013 | Latham et al. |
| 2015/0064769 | A1 * | 3/2015 | Xenopoulos ......... B01D 15/363 435/238 |
| 2019/0071647 | A1 | 3/2019 | Fiadeiro |

FOREIGN PATENT DOCUMENTS

| | | |
|---|---|---|
| CN | 104411820 A | 3/2015 |
| WO | 2012078677 A2 | 6/2012 |
| WO | 2012135415 A1 | 10/2012 |
| WO | 2015158776 A1 | 10/2015 |

OTHER PUBLICATIONS

Bolton et al., "Effect of Protein and Solution Properties on the Donnan Effect During the Ultrafiltration of Proteins", Biotechnol. Prog. 27(1): 140-152 (2011).
Hamers-Casterman et al., "Naturally occurring antibodies devoid of light chains", Nature, 363:446-448 (1993).
Hu et al., "Minibody: A Novel Engineered Anti-Carcinoembryonic Antigen Antibody Fragment (Single-Chain Fv-CH3) Which Exhibits Rapid, High-Level Targeting of Xenografts", Cancer Research, 1996, 56, pp. 3055-3061.
Huston et al., "Protein engineering of antibody binding sites: Recovery of specific activity in an anti-digoxin single-chain Fv analogue produced in *Escherichia coli*", Proceedings of the National Academy of Sciences, USA, 85:5879-5883 (1988).
International Search Report PCT/US2017/021714 completed on May 16, 2017.
Kortt et al., "Single-chain Fv fragments of anti-neuraminidase antibody NC10 containing five- and ten-residue linkers form dimers and with zero-residue linker a trimer", Protein Engineering 10:423-433 (1997).
Leo et al., "Animal Cells: Basic Concepts", Animal Cell Technology: From Biopharmaceuticals to Gene Therapy, 2008, pp. 13-37.
Lovejoy et al., "Crystal Structure of a Synthetic Triple-Stranded a-Helical Bundle", Science, 259:1288-1293 (1993).
Moraes et al., "Culture Media for Animal Cells", Animal Cell Technology: From Biopharmaceuticals to Gene Therapy, 2008, pp. 111-128.
Pack et al., "Improved Bivalent Miniantibodies, with Identical Avidity as Whole Antibodies, Produced by High Cell Density Fermentation of *Escherichia coli*", Biotechnology, 11:1271-1277 (1993).
Pack et al., "Tetravalent Miniantibodies with High Avidity Assembling in *Escherichia coli*Journal of Molecular", Biology, 246:28-34 (1995).
Perisic et al., "Crystal structure of a diabody, a bivalent antibody fragment Structure", Current Biology, 2:1217-1226 (1994).

(Continued)

*Primary Examiner* — Agnieszka Boesen
(74) *Attorney, Agent, or Firm* — Shelley A. Jones

(57) ABSTRACT

Methods for continuously inactivating a virus during manufacture of a protein are provided. Steps include (1) combining, at a single predetermined volumetric ratio, a composition including the protein, and a composition including a virus-inactivation reagent, to obtain a treatment composition having a predetermined property for inactivation of a virus; (2) transferring the treatment composition to a treatment vessel; (3) incubating the treatment composition in the treatment vessel at predetermined conditions; and (4) subjecting the treatment composition to a post-treatment processing operation. The single predetermined volumetric ratio has been selected to ensure that the predetermined property of the treatment composition is maintained across a range of concentrations predicted for the protein in the composition including the protein. Steps (1) to (3) are carried out (a) continuously and (b) without feedback control being exerted by either adjustment of the volumetric ratio or diversion of the treatment composition.

2 Claims, 7 Drawing Sheets

(56) References Cited

OTHER PUBLICATIONS

Po, Henry N. et al. "The Henderson-Hasselbalch Equation: Its History and Limitations" (2001) Journal of Chemical Education, vol. 78, No. 11, 1499-1503.
Sambrook et al., Molecular Cloning: A Laboratory Manual, 2d edition, New York, Cold Spring Laboratory Press (1982).
Shukla et al., Journal of Chromatography, 2007, pp. 28-39.
Tamashiro et al., "Monoclonal Antibodies", Animal Cell Technology: From Biopharmaceuticals to Gene Therapy, 2008, op. 409-433.
Veliz et al., "Bioreactors for Animal Cells", Animal Cell Technology: From Biopharmaceuticals to Gene Therapy, 2008, pp. 221-258.
Ward et al., "Binding activities of a repertoire of single immunoglobulin variable domains secreted from *Escherichia coli*" Nature, 341:544-546 (1989).

\* cited by examiner

METHODS FOR CONTINUOUSLY INACTIVATING A VIRUS DURING MANUFACTURE OF A PROTEIN

FIELD OF THE INVENTION

The present invention relates generally to methods for continuously inactivating a virus during manufacture of a protein, and more particularly, to such methods including steps of (1) combining, at a single predetermined volumetric ratio, a composition including the protein, and a composition including a virus-inactivation reagent, to obtain a treatment composition having a predetermined property for inactivation of a virus; (2) transferring the treatment composition to a treatment vessel; (3) incubating the treatment composition in the treatment vessel at predetermined conditions; and (4) subjecting the treatment composition to a post-treatment processing operation, wherein (i) the single predetermined volumetric ratio has been selected to ensure that the predetermined property of the treatment composition is maintained across a range of concentrations predicted for the protein in the composition including the protein, and (ii) steps (1) to (3) are carried out (a) continuously and (b) without feedback control being exerted by either adjustment of the volumetric ratio or diversion of the treatment composition.

BACKGROUND OF THE INVENTION

Inactivation of viruses that may be present in a composition including a protein that is intended for use in a biopharmaceutical product, such as a therapeutic antibody, is an important aspect of quality control for ensuring that the biopharmaceutical product will work as intended and will not inadvertently cause disease or other harm. Viral contamination can occur during the production of a protein, through both exogenous and endogenous sources. Viruses can be difficult to detect, given the diversity of their structures and genomes, and, once present, can be difficult to physically remove due to their small size. To account for the possibility of viral contamination, industrial processes for production of proteins typically include one or more steps for inactivation of potential viral contaminants.

Typical methods from the state of the art include adding a virus-inactivation reagent, such as an acid or a detergent, to a composition including a protein, mixing thoroughly, incubating for a specific time, then neutralizing or removing the virus-inactivation reagent, all done in a discontinuous mode, i.e. batch mode, to accomplish inactivation of viruses that may be present in the composition including the protein, as taught, for example by Ristol Debart et al., U.S. Pat. No. 6,875,848, Shadle et al., U.S. Pat. No. 5,429,746, and Latham et al, U.S. Pub. No. 2013/0236358. In accordance with such methods, inactivation of the viruses that may be present may require multiple discontinuous steps and/or extended incubation times, though, during which time the composition including the protein typically is not otherwise processed, potentially adding substantial time to the overall process for manufacturing the protein.

Other methods include treating a composition including a protein with a dose of light, such as monochromatic or polychromatic light, in a continuous mode, e.g. as the composition flows through a thin-layer irradiator, optionally with mixing to narrow residence time distribution and increase inactivation rate, in order to accomplish inactivation of microorganisms that may be present in the composition, as taught, for example, by Anderle et al., U.S. Pat. No. 7,993,580. Control of the dose of light may be difficult, though, as the dose can vary across the composition depending on factors such as micro-heterogeneities in absorbance and rate of flow of the composition during irradiation, and can vary across time depending on aging of corresponding light sources and fluctuations in light emissions.

Other methods include mixing a composition including a protein with a virus-inactivation reagent, such as an acid or a detergent, continuously, e.g. using one or more in-line static mixers, during flow from a first unit operation to a second unit operation, in order to inactivate viruses that may be present in the composition, with residence time for virus inactivation being altered by having tubes of appropriate diameter and length after each static mixer and before a pH probe, as taught, for example, by Xenopoulos, U.S. Pub. No. 2015/0064769. A problem with such methods, though, is that the methods essentially include performance of batch titration based on a pH feedback loop and are dependent on proper function of pH meters for adjustment and maintenance of pH at a low and optimal range suitable for inactivation of virus. This makes the methods unstable and susceptible to rapid and uncontrolled fluctuations of pH, which can negatively affect inactivation of the virus and thus quality of the corresponding protein.

Other methods include steps of continuously combining a composition including a biological product and a composition including a virus-inactivation reagent, to obtain a treatment composition having a predetermined property for inactivation of a virus, confirming that the treatment composition exhibits the predetermined property, transferring the treatment composition to a treatment vessel that includes a static mixer, incubating the treatment composition in the treatment vessel at a predetermined temperature while the treatment composition flows at a predetermined rate and contacts the static mixer, and collecting the treatment composition from the treatment vessel, wherein the steps are carried out continuously, as taught, for example, by Coffman et al., WO 2015/158776. Such methods may include a control burden that could be eliminated, though, for example to the extent that the step of confirming that the treatment composition exhibits the predetermined property is carried out for purposes of feedback control, e.g. to allow diversion of treatment composition that may not exhibit the predetermined property.

Accordingly, a need exists for improved methods for continuously inactivating a virus during manufacture of a protein.

BRIEF SUMMARY OF THE INVENTION

In a first aspect of the disclosure, a method for continuously inactivating a virus during manufacture of a protein is provided. The method includes a step of (1) combining, at a single predetermined volumetric ratio, (a) a composition including the protein, and (b) a composition including a virus-inactivation reagent, to obtain (c) a treatment composition having a predetermined property for inactivation of a virus. The method also includes a step of (2) transferring the treatment composition to a treatment vessel. The method also includes a step of (3) incubating the treatment composition in the treatment vessel at predetermined conditions. The method also includes a step of (4) subjecting the treatment composition to a post-treatment processing operation. In accordance with the method, the single predetermined volumetric ratio has been selected to ensure that the predetermined property of the treatment composition is maintained across a range of concentrations predicted for the protein in the composition including the protein. Also in accordance with the method, steps (1) to (3) are carried out (a) continuously and (b) without feedback control being exerted by either adjustment of the volumetric ratio or diversion of the treatment composition.

Without wishing to be bound by theory, it is believed that by selecting the single predetermined volumetric ratio to ensure that the predetermined property of the treatment composition is maintained across a range of concentrations predicted for the protein in the composition including the protein, and by carrying out steps (1) to (3) continuously and without feedback control being exerted by either adjustment of the volumetric ratio or diversion of the treatment composition, inactivation of virus during manufacture of a protein can be carried out in a stable manner without need for confirming that the treatment composition exhibits the predetermined property as inactivation of the virus is being carried out, allowing elimination of a control burden associated with feedback control during the inactivation of the virus.

In a second aspect of the disclosure, a method for inactivating one or more viruses in a sample is provided. The method includes continuously mixing the sample with one or more virus-inactivating reagents as the sample flows from a first unit operation to a second unit operation during a process for purifying a target molecule. In accordance with the method, the ratio of the one or more virus-inactivating reagents to the sample is determined independently of, or without, a feedback control mechanism.

Without wishing to be bound by theory, it also is believed that by continuously mixing a sample with one or more virus-inactivating reagents as the sample flows from a first unit operation to a second unit operation during a process for purifying a target molecule, in accordance with the principles and approaches disclosed herein, including that the ratio of the one or more virus-inactivating reagents to the sample is determined independently of, or without, a feedback control mechanism, that inactivation of the one or more viruses can be accomplished to an extent sufficient for purposes of manufacturing biopharmaceutical products, also allowing elimination of a control burden associated with feedback control during the inactivation of the one or more viruses.

BRIEF DESCRIPTION OF THE DRAWINGS

These and other features, aspects, and advantages of the claimed methods, apparatuses, and systems are better understood when the following detailed description is read with reference to the accompanying drawings, in which:

DETAILED DESCRIPTION OF THE INVENTION

Figure 1:
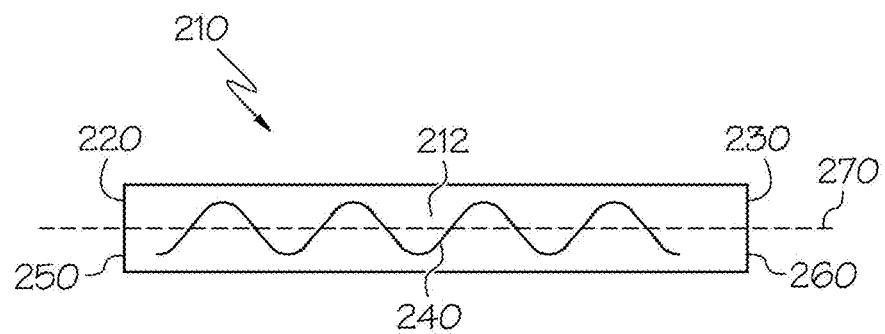
FIG. 1 is a schematic view of an example treatment vessel 210 for use in a method for continuously inactivating a virus during manufacture of a protein, in which the example treatment vessel 210 has a linear shape.

Aspects of the claimed methods will now be described more fully hereinafter with reference to the accompanying drawings in which example embodiments are shown. Whenever possible, the same reference numerals are used throughout the drawings to refer to the same or like parts. However, the claimed methods may be embodied in many different forms and should not be construed as limited to the embodiments set forth herein. These example embodiments are provided so that this disclosure will be both thorough and complete, and will fully convey the scope of the claimed methods to those skilled in the art.

A method for continuously inactivating a virus during manufacture of a protein is provided. As noted above, inactivation of viruses that may be present in a composition including a protein that is intended for use in a biopharmaceutical product is an important aspect of quality control. The protein can be, for example, a therapeutic protein, such as an antibody, an antibody fragment, an antibody derivative, a cytokine, a growth factor, a hormone, an enzyme, or a blood coagulation factor, among others, or a vaccine protein, such as an antigenic protein, among others. The protein can be produced by a living system, such as a cell, tissue, or organism, e.g. by a mammalian cell, a plant cell, or a bacterial cell, among others. The protein can be produced by a homogeneous process, e.g. suspension culture based on use of a stirred-tank bioreactor, air-lift bioreactor, or wave bioreactor, or a heterogeneous process, e.g. adherent culture based on a microcarrier-based system, a packed bed bioreactor, or a hollow-fiber bioreactor, as carried out in a discontinuous mode, e.g. batch cultivation or fed-batch cultivation, or in a continuous mode, e.g. continuous cultivation with perfusion, and as carried out at any suitable scale, e.g. laboratory, pilot, or production scale. The virus may be one that can infect bacteria (i.e. a "bacteriophage," also termed a "phage"), or a human and/or an animal, e.g. the individual human or animal for which the protein is intended for administration, among others. The virus may have been introduced into the composition including the protein from an exogenous source, e.g. by inadvertent failure to maintain sterility, or from an endogenous source, e.g. the living system used to make the protein.

The method can be used to ensure that a virus that may have been present during the manufacture of the protein, for example based on viral contamination, is inactivated. To the extent that multiple different types of viruses and/or multiple active particles of a given type of virus may be present, the method can be used to inactivate the multiple different types and/or multiple active particles of a given type. Thus, for example, the method can be used to ensure that a biopharmaceutical product that ultimately includes the protein will not include active particles of virus of any type in any amount above an acceptable limit, e.g. that the biopharmaceutical product will be free of active particles of virus.

The method includes a step of (1) combining, at a single predetermined volumetric ratio, (a) a composition including the protein, and (b) a composition including a virus-inactivation reagent, to obtain (c) a treatment composition having a predetermined property for inactivation of a virus.

The composition including the protein can be, for example, a composition derived directly from a bioreactor, e.g. a bioreactor being used for production of the protein by a living system such as a mammalian cell culture. The composition including the protein can be, for example, one obtained from a bioreactor being operated in a continuous mode, e.g. continuous cultivation with perfusion, and thus can include a cell culture medium, having been utilized to some extent by cells of a mammalian cell culture, and the protein, as secreted from the cells. The composition including the protein also can be, for example, a composition derived indirectly from a bioreactor, e.g. following one or more processing operations, such as filtration, precipitation, and/or chromatographic separation, among other steps, to remove some or all unwanted debris, compounds, and other substances prior to subjecting the composition including the protein to the method for continuously inactivating a virus. In such cases, the processing operation can correspond to a pre-treatment processing operation, meaning that steps for inactivation of virus, as disclosed herein, will be carried out after the processing operation.

Accordingly, the composition including the protein can be obtained from a pre-treatment processing operation. The pretreatment-processing operation can correspond to a processing operation for obtaining the composition including the protein, as separated from unwanted debris, compounds, and/or other substances, e.g. that may be present with the protein as the protein is initially obtained from a bioreactor. The pre-treatment processing operation can include, for example, filtration, precipitation, and/or chromatographic separation, among other processing operations. Thus, the composition including the protein can include, for example, a filtrate including the protein, e.g. for a pre-treatment processing operation that is filtration, a precipitate including the protein, e.g. for a pre-treatment processing operation that is precipitation, and/or a chromatographic eluate, e.g. for a pre-treatment processing operation that is chromatographic separation, among other types of compositions.

Regarding chromatographic separation in particular, the pre-treatment processing operation can include, for example, immunoglobulin-binding protein affinity chromatography. Immunoglobulin-binding protein chromatography is useful for purifying immunoglobulins, including for example an antibody, antibody fragment, or antibody derivative, among other immunoglobulins. Immunoglobulin-binding proteins suitable for immunoglobulin-binding protein chromatography include, for example, Protein A, Protein G, Protein A/G, and Protein L. Protein A in particular is available in native and recombinant forms and has high affinity for the Fragment crystallizable (also termed Fc) fragment of immunoglobulin G. Immunoglobulin-binding protein chromatography can be carried out, for example, based on immobilization of the immunoglobulin-binding protein to a solid support, such as, for example, crosslinked beaded agarose, polyacrylamide, or other porous solid supports. Thus, for example, the pre-treatment processing operation can include, for example, Protein A antibody affinity chromatography, Protein G antibody affinity chromatography, Protein A/G antibody affinity chromatography, and/or Protein L antibody affinity chromatography.

As noted above, the method includes a step of (1) combining, at a single predetermined volumetric ratio, (a) a composition including the protein, and (b) a composition including a virus-inactivation reagent, to obtain (c) a treatment composition having a predetermined property for inactivation of a virus.

The predetermined property of the treatment composition for inactivation of a virus can include at least one of a pH between 3.0 to 3.8 or a detergent concentration between 0.05% and 10% (v/v) (v/v referring to detergent volume per final volume in the case of detergents). A pH between 3.0 to 3.8 can cause inactivation of virus, without harming the protein. Likewise, a detergent concentration between 0.05% and 10% (v/v) can cause inactivation of virus, without harming the protein. The predetermined property can be predetermined in the sense that an overall process that is sufficient to accomplish inactivation of virus in a treatment composition to a desired extent can be developed, based on preparing a treatment composition having a specific property for inactivation of a virus and testing various conditions to determine and confirm sufficiency, followed by application of the process during manufacture of the protein generally. Such application can include combining a composition including the protein and a composition including the virus-inactivation reagent to obtain a treatment composition having the predetermined property for inactivation of a virus, i.e. the method can be carried out in accordance with a specific plan to ensure inactivation of a virus that may be present. Thus, in some examples the predetermined property of the treatment composition includes a pH between 3.0 to 3.8, e.g. 3.3 to 3.7, or 3.4 to 3.6. In some examples the predetermined property of the treatment composition includes a detergent concentration between 0.05% and 10% (v/v), e.g. between 0.05% and 5.0% (v/v), or between 0.05% and 2.0% (v/v). In some examples the predetermined property of the treatment composition includes both a pH between 3.0 to 3.8 and a detergent concentration between 0.05% and 10% (v/v), for example a pH between 3.3 to 3.7 and a detergent concentration between 0.05% and 5.0%

(v/v), or a pH between 3.3 to 3.7 and a detergent concentration between 0.05% and 2.0% (v/v), or a pH between 3.4 to 3.6 and a detergent concentration between 0.05% and 5.0% (v/v), or a pH between 3.4 to 3.6 and a detergent concentration between 0.05% and 2.0% (v/v).

The virus-inactivation reagent can include, for example, at least one of (a) an acid having a titratable group having a pKa between 2.3 to 4.2 and not having another titratable group having a pKa between 4.2 and 8.5, (b) acetic acid, or (c) a non-ionic detergent having a chromophoric group having an absorption peak between 230 nm and 600 nm.

An acid having a titratable group having a pKa between 2.3 to 4.2 and not having another titratable group having a pKa between 4.2 and 8.5 means an acid that has at least one titratable group that has a pKa between 2.3 and 4.2, and that may have additional titratable groups having a pKa below 2.3 or above 8.5, but that does not have another titratable group that has a pKa between 4.2 and 8.5, each pKa as determined at about 20 to 25° C.

An organic acid, such as for example a carboxylic acid or an amino acid, having a pKa between 2.3 to 4.2 and not having another titratable group having a pKa between 4.2 and 8.5 is such an acid. Such organic acids include, for example, lactic acid, which has a titratable group having a pKa of 3.86 at 25° C., and which does not have another titratable group having a pKa between 4.2 and 8.5. Formic acid, which has a titratable group having a pKa of about 3.74 at 20° C., and which does not have another titratable group having a pKa between 4.2 and 8.5, also is such an organic acid. Ascorbic acid, which has a titratable group having a pKa of 4.17 at about 20 to 25° C. and an additional titratable group that has a pKa of 11.6 also at about 20 to 25° C., and which does not have another titratable group having a pKa between 4.2 and 8.5, also is such an organic acid. Glycine, which has a titratable group having a pKa of 2.34 at about 20 to 25° C., and which does not have another titratable group having a pKa between 4.2 and 8.5, also is such an organic acid. Thus, for example, the virus-inactivation reagent can be an acid having a titratable group having a pKa between 2.3 to 4.2 and not having another titratable group having a pKa between 4.2 and 8.5 selected from the group consisting of an organic acid having a titratable group having a pKa between 2.3 to 4.2 and not having another titratable group having a pKa between 4.2 and 8.5, lactic acid, formic acid, ascorbic acid, an amino acid having a titratable group having a pKa between 2.3 to 4.2 and not having another titratable group having a pKa between 4.2 and 8.5, glycine, or a combination thereof.

The acid having a titratable group having a pKa between 2.3 to 4.2 and not having another titratable group having a pKa between 4.2 and 8.5 can be useful in the method for at least the following reasons. First, by having a titratable group having a pKa between 2.3 to 4.2, the acid can adequately buffer the treatment composition at a pH between 3.0 to 3.8 without need for including high amounts of the acid, e.g. the acid can be present in the treatment composition at or below 100 mM and still provide sufficient buffering capacity. This can ensure maintenance of the treatment composition at a pH between 3.0 to 3.8, the pH being low enough to enable inactivation of virus, but high enough to avoid harm to the protein, e.g. acid denaturation of protein. Second, by not having another titratable group having a pKa between 4.2 and 8.5, the treatment composition including the acid can later be neutralized without need for titration of another titratable group, and thus without need for addition of extra ions that would not otherwise need to be added in the absence of the other titratable group. This can promote effectiveness of any ion exchange step that may be carried out following inactivation of the virus.

Certain particular acids having a titratable group having a pKa between 2.3 to 4.2 and not having another titratable group having a pKa between 4.2 and 8.5 also can be useful for additional reasons. For example, lactic acid is additionally useful because it is naturally present in cells and thus in processes for production of proteins, it is a substance that is Generally Recognized as Safe (also termed "GRAS") by the FDA, and it is inexpensive.

Acetic acid, which has a titratable group having a pKa of 4.74 at about 20 to 25° C., and which does not have another titratable group, also can be useful in the method.

A non-ionic detergent having a chromophoric group having an absorption peak between 230 nm and 600 nm includes, for example, a polyethylene oxide detergent having an aromatic group, among others, which includes for example Triton-X 100 detergent, among others. Thus, for example, the virus-inactivation reagent can be a non-ionic detergent having a chromophoric group having an absorption peak between 230 nm and 600 nm selected from the group consisting of a polyethylene oxide detergent having an aromatic group, Triton-X 100 detergent, and combinations thereof.

The non-ionic detergent having a chromophoric group having an absorption peak between 230 nm and 600 nm can be useful in the method for at least the following reasons. First, if the non-ionic detergent is present in the treatment composition at a suitable concentration, the uncharged hydrophilic groups of the non-ionic detergent can be used to inactivate virus without harming the protein. Second, the chromophoric group having an absorption peak between 230 nm and 600 nm of the non-ionic detergent can be used for measuring the detergent concentration, e.g. within the composition including the virus-inactivation reagent and/or within the treatment composition, for example based on ultraviolet absorption by the chromophoric group, which is a concentration-dependent characteristic.

Thus, for example, the composition including the virus-inactivation reagent can be a composition that includes at least one of (a) an acid having a titratable group having a pKa between 2.3 to 4.2 and not having another titratable group having a pKa between 4.2 and 8.5, or (b) acetic acid, or (c) a non-ionic detergent having a chromophoric group having an absorption peak between 230 nm and 600 nm, e.g. the composition can include one or more of the acids as recited, one or more of the non-ionic detergents as recited, or combinations thereof.

Also for example, the virus-inactivation reagent can be an acid having a titratable group having a pKa between 2.3 to 4.2 and not having another titratable group having a pKa between 4.2 and 8.5 selected from the group consisting of an organic acid having a titratable group having a pKa between 2.3 to 4.2 and not having another titratable group having a pKa between 4.2 and 8.5, lactic acid, formic acid, ascorbic acid, an amino acid having a titratable group having a pKa between 2.3 to 4.2 and not having another titratable group having a pKa between 4.2 and 8.5, glycine, or a combination thereof, and the predetermined property can include a pH between 3.0 to 3.8. In accordance with this example, the predetermined property can include a pH between 3.3 to 3.7. Also in accordance with this example, the predetermined property can include a pH between 3.4 to 3.6.

Also for example, the virus-inactivation reagent can be acetic acid, and the predetermined property can include a pH between 3.0 to 3.8. In accordance with this example, the predetermined property can include a pH between 3.3 to 3.7.

Also in accordance with this example, the predetermined property can include a pH between 3.4 to 3.6.

Also for example, the virus-inactivation reagent can be a non-ionic detergent having a chromophoric group having an absorption peak between 230 nm and 600 nm selected from the group consisting of a polyethylene oxide detergent having an aromatic group, Triton-X 100 detergent, and combinations thereof, and the predetermined property can include a detergent concentration between 0.05% and 10% (v/v).

Again, as noted, the method includes a step of (1) combining, at a single predetermined volumetric ratio, (a) a composition including the protein, and (b) a composition including a virus-inactivation reagent, to obtain (c) a treatment composition having a predetermined property for inactivation of a virus. The effectiveness of the virus-inactivation reagent for inactivating virus that may be present will depend on the concentration of the virus-inactivation reagent in the treatment composition, among other factors. The concentration of the virus-inactivation reagent necessary to inactivate a virus to a given extent can be determined empirically under actual conditions, estimated based on prior experience under analogous conditions, and/or predicted based on theory. As will further be appreciated, this concentration also can be used to ensure that the virus-inactivation reagent is included in the composition including the virus-inactivation reagent at a suitable concentration to ensure, upon taking into account the proportional contribution of the composition including the virus-inactivation reagent to the volume of the treatment composition, that the virus-inactivation reagent will be present in the treatment composition at a concentration effective for inactivation of virus. For example, considering use of a virus-inactivation reagent corresponding to one of the acids recited, e.g. lactic acid, if it is determined that the acid should be included in the treatment composition at about 100 mM, and the treatment composition will be prepared by combining about one volume of the composition including the virus-inactivation reagent per nine volumes of the composition including the protein, then the composition including the virus-inactivation reagent can be prepared including the acid at a concentration of about 1 M. Also for example, considering use of a virus-inactivation reagent corresponding to one of the non-ionic detergents recited, e.g. Triton-X 100 detergent, if it is determined that the non-ionic detergent should be included in the treatment composition at about 1.0% (v/v) (again v/v referring to detergent volume per final volume in the case of detergents), and the treatment composition will be prepared by combining about one volume of the composition including the virus-inactivation reagent per nine volumes of the composition including the protein, then the composition including the virus-inactivation reagent can be prepared including the non-ionic detergent at a concentration of about 10% (v/v).

As noted, in accordance with step (1) the composition including the protein and the composition including the virus-inactivation reagent are combined to obtain a treatment composition having a predetermined property for inactivation of a virus. The combining can be carried out, for example, within a vessel including one or more mixers, such that the composition including the protein and the composition including the virus-inactivation reagent are added to the vessel, e.g. separately and simultaneously, flow through the vessel, e.g. under pressure, and are mixed while flowing, e.g. by the one or more mixers. The mixing can occur, for example, for a period of time, e.g. 1 to 5 minutes, that is sufficiently long to ensure that the treatment composition is mixed to homogeneity, but not so long as for inactivation of the virus to proceed to a substantial extent. Other approaches also can be used, e.g. the combining can be carried out without use of one or more mixers, and/or the combining can be carried out for a longer period of time or a shorter period of time, among other approaches.

Also as noted, in accordance with step (1), the composition including the protein and the composition including the virus-inactivation reagent are combined at a single predetermined volumetric ratio. This means that the composition including the protein and the composition including the virus-inactivation reagent are combined at a ratio of volume of the composition including the protein and volume of the composition including the virus-inactivation reagent that has been determined in advance to be suitable for carrying out the method, as discussed in more detail below.

The method also includes a step of (2) transferring the treatment composition to a treatment vessel. The treatment vessel can be a vessel suitable for continuous inactivation of virus. The transferring of the treatment composition to the treatment vessel can occur, for example, based on the treatment composition flowing under pressure to the treatment vessel.

Figure 2:
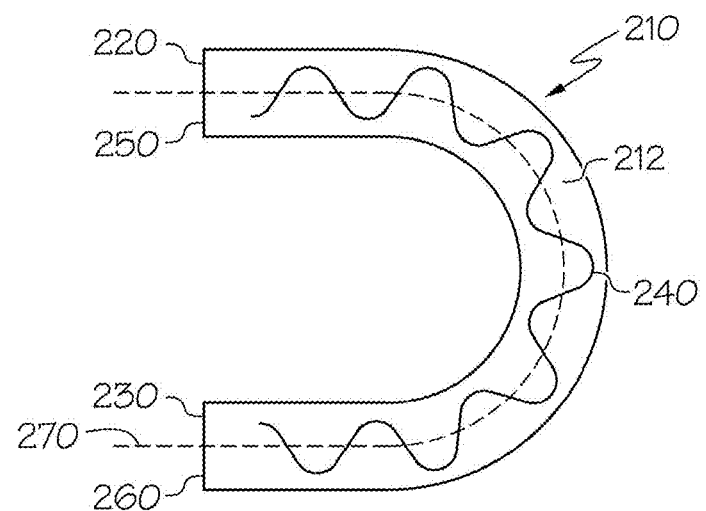
FIG. 2 is a schematic view of an example treatment vessel 210 for use in a method for continuously inactivating a virus during manufacture of a protein, in which the example treatment vessel 210 has a curved shape.
Figure 3:
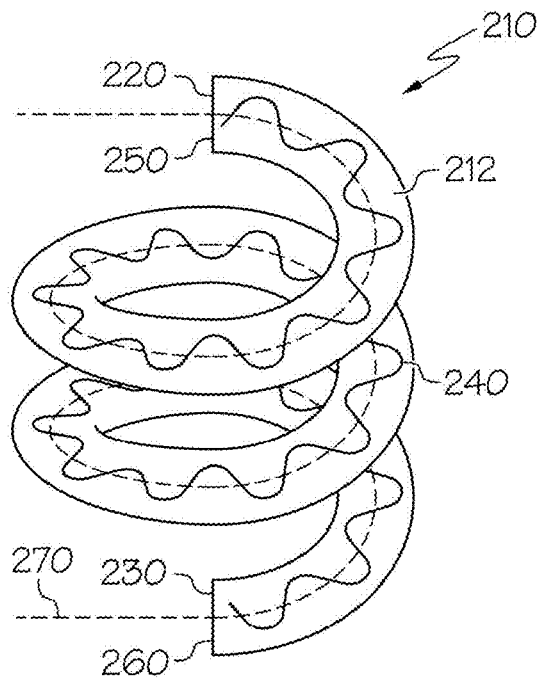
FIG. 3 is a schematic view of an example treatment vessel 210 for use in a method for continuously inactivating a virus during manufacture of a protein, in which the example treatment vessel 210 has a spiral shape.

Considering the treatment vessel in more detail, with reference to FIG. 1, an example treatment vessel 210 is provided. The example treatment vessel 210 includes an inlet 220, an outlet 230, and a static mixer 240 and having an internal volume 212, the inlet 220 and the outlet 230 being positioned at opposite ends, i.e. an inlet end 250 and an outlet end 260, of a major axis 270 of the example treatment vessel 210 and the static mixer 240 being internal to the example treatment vessel 210 along the major axis 270. In accordance with this example, step (2) can include transferring the treatment composition to the example treatment vessel 210, with the transferring occurring at the inlet 220. As shown in FIG. 1, the treatment vessel 210 can be in the form of, for example, a column or a tube, among other forms. As shown in FIG. 1, FIG. 2, and FIG. 3, respectively, the example treatment vessel 210 can have a shape that is, for example, linear, curved, or spiral, among other shapes, and thus can have a major axis 270 that also is, for example, linear, curved, or spiral, among other types. The example treatment vessel 210 can be made from, for example, a metal, a plastic, or a combination thereof, among other materials. The treatment vessel can include one static mixer 240, or multiple static mixers 240, e.g. two, three, four, or more, as appropriate to ensure effective mixing. The static mixer can be a type of static mixer that includes, for example, baffles, orifices, impingement plates, and/or other in-line protuberances. The static mixer can be made of one or more materials that are compatible with biopharmaceutical processing, e.g. one or more of metal, plastic, rubber, and/or glass compatible with biopharmaceutical processing. Other treatment vessels also can be used.

Considering the transferring of the treatment composition to the treatment vessel in more detail, the transferring can be from a vessel including one or more mixers, as described above, to the treatment vessel, with the vessel including one or more mixers and the treatment vessel being fluidically connected, i.e. connected such that a fluid can flow internally and at least unidirectionally from the vessel including one or more mixers to the treatment vessel. The rate of the transferring can be controlled, e.g. by a pump.

The method also includes a step of (3) incubating the treatment composition in the treatment vessel at predetermined conditions. To the extent that a virus is present in the treatment composition prior to step (3), e.g. as multiple different types of viruses and/or multiple active particles of a given type of virus, the virus will be inactivated to at least some extent based on incubation in the treatment vessel during step (3).

The predetermined conditions can be a combination of conditions, such a predetermined temperature and a predetermined time of incubation of the treatment composition in the treatment vessel, useful for inactivation of a virus. For incubation of the treatment composition that includes flow of the treatment composition in the treatment vessel, a predetermined time of incubation can be reflected based on a rate of flow of the treatment composition in the treatment vessel.

Thus, for example, the treatment vessel can be maintained at a predetermined temperature, for example, by use of a heating element, and the flow of the treatment composition can be maintained at a predetermined rate, for example, by use of a pump. Also for example, the predetermined temperature and the predetermined rate can be predetermined in the sense that an overall process sufficient to accomplish inactivation of virus to a desired extent can be developed, based on incubating the treatment composition in the treatment vessel at a specific temperature and for a specific time and testing various conditions to determine and confirm sufficiency, followed by application of the process during manufacture of the protein generally, including controlling the temperature of the treatment vessel and controlling the rate of flow of the treatment composition through the treatment vessel in order to ensure that the treatment composition is subjected to a treatment sufficient to accomplish inactivation of the virus to a desired extent. Again, the method can be carried out in accordance with a specific plan to ensure inactivation of virus that may be present.

Also for example, the predetermined conditions can include a predetermined temperature between 17 and 40° C. and a predetermined rate of flow of the treatment composition through the treatment vessel that is 0.3 to 3 times an internal volume of the treatment vessel per hour. In general, as the predetermined temperature is increased, the predetermined rate can also be increased, and vice versa. Conversely, as the predetermined temperature is decreased, the predetermined rate may need to be decreased, and vice versa. This is because the virus-inactivation reagent typically can inactivate virus in the treatment composition more rapidly at a higher temperature, and thus the treatment composition can be incubated in the treatment vessel for a shorter time while still accomplishing inactivation of the virus to a desired extent. For example, the predetermined temperature can be between 18 and 25° C. and the predetermined rate can be 0.5 to 1.5 times the internal volume of the treatment vessel per hour. Also for example, the predetermined temperature can be between 30 and 39° C. and the predetermined rate can be 0.8 to 2.0 times the internal volume of the treatment vessel per hour.

The predetermined conditions can be sufficient to cause inactivation of the virus in the treatment composition by the virus-inactivation reagent during step (3) by a factor of at least $1\times10^1$. For example, the predetermined conditions can be sufficient to cause inactivation of the virus in the treatment composition by the virus-inactivation reagent during step (3) by a factor of at least $1\times10^2$, at least $1\times10^3$, at least $1\times10^4$, at least $1\times10^5$, or at least $1\times10^6$. In accordance with this example, the predetermined conditions can be sufficient to cause inactivation of the virus in the treatment composition by the virus-inactivation reagent to at least the extent indicated under a condition of actual viral contamination, as well as under a condition for which viral contamination may be present, whether or not viral contamination is actually present. Moreover, the sufficiency of the predetermined conditions to cause inactivation of the virus can relate to inactivation with respect to a specific type of virus, multiple specific types of viruses, and/or a general or diverse range of viruses. In addition, the sufficiency of the predetermined conditions to cause inactivation of the virus can relate to inactivation with respect to only a portion of the treatment composition subjected to incubation during step (3), e.g. to a portion of the treatment composition incubated in the treatment vessel during a part of the period that the method is being carried out, or to all of the treatment composition subjected to incubation during step (3), e.g. all of the treatment composition so incubated during the entire period that the method is carried out, from start to finish.

Also for example, the internal volume of the treatment vessel can be sufficiently large to ensure that not more than one part per million of the treatment composition has a residence time in the treatment vessel of a shorter duration than that required to cause inactivation of the virus in the treatment composition by the virus-inactivation reagent during step (3) by a factor of at least $1\times10^1$. In this regard, the treatment vessel can be made or selected based on having an internal volume that is sufficiently large to account for axial dispersion of the treatment composition as the treatment composition flows through the treatment vessel, i.e. dispersion of the treatment composition along the major axis of the treatment vessel, to control and minimize proportions of the treatment composition that can flow through treatment vessel in less time than would be required to cause inactivation of the virus in the treatment composition by the virus-inactivation reagent during step (3) by a factor of at least $1\times10'$. For example, the treatment vessel can be made or selected based on having an internal volume that includes an extra volume beyond a theoretical plug flow volume in order to account for axial dispersion. The theoretical plug flow volume Vh* of a vessel can be calculated as the product of the critical hold time Tr and the volumetric flow rate Q of a composition within the vessel. The extra volume necessary to account for axial dispersion can be estimated, for example, by using the Taylor dispersion model for laminar flow, or a plug flow, a Gaussian model for turbulent flow, or a model developed specifically for a given static mixer, among other approaches. Thus, for example, the internal volume of the treatment vessel can be sufficiently large to ensure that not more than one part per million of the treatment composition, e.g. not more than one part per ten million, one part per hundred million, or one part per billion, has a residence time in the treatment vessel of a shorter duration than that required to cause inactivation of the virus in the treatment composition by the virus-inactivation reagent during step (3) by a factor of at least $1\times10'$, e.g. by a factor of at least $1\times10^2$, at least $1\times10^3$, at least $1\times10^4$, at least $1\times10^5$, or at least $1\times10^6$. Also for example, the internal volume of the treatment vessel can be sufficiently large to ensure that not more than one part per million of active particles of virus in the treatment composition, e.g. not more than one part per ten million, one part per hundred million, or one part per billion, has a residence time in the treatment vessel of a shorter duration than that required to cause inactivation of the virus in the treatment composition by the virus-inactivation reagent during step (3) by a factor of at least $1\times10'$, e.g. by a factor of at least $1\times10^2$, at least $1\times10^3$, at least $1\times10^4$, at least $1\times10^5$, or at least $1\times10^6$.

Considering again the example treatment vessel 210 as discussed above, as noted, the treatment composition contacts the static mixer 240 as the treatment composition flows along the major axis 270 of the treatment vessel 210, e.g. including contacting multiple static mixers 240 for treatment vessels 210 that include multiple static mixers 240. This contacting provides for continuous mixing of the treatment composition as the treatment composition flows through the treatment vessel 210, thus minimizing axial dispersion of the treatment composition. Thus, in some examples step (3) includes incubating the treatment composition in the example treatment vessel 210 at a predetermined temperature while the treatment composition flows along the major axis 270 at a predetermined rate and contacts the static mixer 240, the combination of the predetermined temperature and the predetermined rate being sufficient to cause inactivation of the virus in the treatment composition based on the predetermined property.

Other approaches also can be used.

The method also includes a step (4) of subjecting the treatment composition to a post-treatment processing operation. Analogously as for the pre-treatment processing operation, the post-treatment processing operation can correspond to a processing operation for obtaining a now-treated composition including the protein, as separated from unwanted debris, compounds, and/or other substances, e.g. that may be present with the protein in the treatment composition. The post-treatment processing operation can include, for example, filtration, precipitation, and/or chromatographic separation, among other processing operations. Thus, for example, the post-treatment processing operation can include one or more of anion exchange chromatography, cation exchange chromatography, or passage through viral filtration media.

Regarding anion exchange chromatography, like immunoglobulin-binding protein chromatography, anion exchange chromatography also is useful for purifying immunoglobulins, including for example an antibody, antibody fragment, or antibody derivative, among other immunoglobulins. Anion exchange groups suitable for anion exchange chromatography include, for example, diethylaminoethyl (also termed DEAE) groups, polyethyleneimine (also termed PEI) groups, and quarternary ammonium (also termed Q) groups. Anion exchange groups can be used, for example, as a final step (also termed a polishing step) for purification of a protein based on suitable resolution and speed. Anion exchange chromatography also can be carried out, for example, based on presence of anion exchange groups on a solid support. Thus, for example, the post-treatment processing operation can include, for example, diethylaminoethyl anion exchange chromatography, polyethyleneimine anion exchange chromatography, or quarternary ammonium anion exchange chromatography.

For purposes of subjecting the treatment composition to a post-treatment processing operation in accordance with step (4), the treatment composition can be obtained from the treatment vessel, for example, by collecting the treatment composition from the treatment vessel. The collecting can correspond to, for example, allowing the treatment composition to flow from the treatment vessel to another vessel, e.g. for neutralization or removal of the virus-inactivation reagent, for further inactivation of virus, for storage prior to the treatment composition being subjected to the post-treatment processing operation, and/or directly to be subjected to the post-treatment processing operation.

Considering again the example treatment vessel 210 as discussed above, as noted, the treatment composition can be collected from the example treatment vessel 210 at the outlet 230, and then subjected to a post-treatment processing operation in accordance with step (4).

In accordance with the method, the single predetermined volumetric ratio has been selected to ensure that the predetermined property of the treatment composition is maintained across a range of concentrations predicted for the protein in the composition including the protein. As noted above, the composition including the protein and the volume of the composition including the virus-inactivation reagent are combined at a ratio of volume of the composition including the protein and volume of the composition including the virus-inactivation reagent that has been determined in advance of carrying out the method. Specifically, the single predetermined volumetric ratio has been selected to ensure that the predetermined property of the treatment composition is maintained across a range of concentrations predicted for the protein in the composition including the protein, without need for varying the volumetric ratio in response to variation in the concentration of the protein, and thus without need for using volumetric ratios other than the single predetermined volumetric ratio.

Surprisingly, it has been determined that the concentration of virus-inactivation reagent that is needed for inactivation of virus in a treatment composition that includes a monoclonal antibody of a Protein A eluate is primarily driven by concentration of the monoclonal antibody. Accordingly, by determining a range of concentrations predicted for a protein in a composition including the protein, e.g. a range of concentrations predicted for the protein in sequential fractions of eluate from immunoglobulin-binding protein affinity chromatography, that will be combined with a composition including the virus-inactivation reagent, to obtain the treatment composition, and by ensuring that the concentration of the protein will not substantially exceed an upper limit of the range, the steps for continuous inactivation of virus can be carried out without need for feedback control being exerted by either adjustment of the volumetric ratio or diversion of the treatment composition.

Put another way, the method can be carried out with chemical control, meaning, with use of a composition including a virus-inactivation reagent, to maintain a treatment composition having a predetermined concentration of the virus-inactivation reagent and/or pH within a tight window for incoming protein streams. The method can rely physically on pump metering of two or more solutions, e.g. the composition including the protein and the composition including the virus-inactivation reagent, to achieve the predetermined concentration of the virus-inactivation reagent and/or pH, rather than relying on active or dynamic feedback from probes or a proportional-integral-derivative (also termed PID) control loop based on output, i.e. monitoring of the treatment composition. The ratio of volume of the composition including the protein and volume of the composition including the virus-inactivation reagent is predetermined with a priori knowledge of the key factors in the process. Accordingly, physical control of the process, e.g. for pump metering, can be preset, and a single volumetric ratio can be used throughout the method, despite variations in concentration of the protein in the composition including the protein as the method is being carried out.

Considering an example of the method including use of a virus-inactivation reagent including an acid, e.g. an acid having a titratable group having a pKa between 2.3 to 4.2 and not having another titratable group having a pKa between 4.2 and 8.5, and/or acetic acid, and including a pre-treatment processing operation including Protein A antibody affinity chromatography, the method solves the problems discussed above by a treatment composition, including the Protein A eluate, as combined with the composition including the virus-inactivation reagent, within a tight and uniform pH range of 3.3 to 3.7 as the treatment composition flows in-line from one unit operation to the next, e.g. from a pre-treatment processing operation to a post-treatment processing operation, so that virus inactivation is achieved accurately and efficiently without reliance on pH meters. The method can include determining a priori which virus-inactivation reagent will provide the most efficient inactivation of virus for a given protein. The virus-inactivation reagent can then be added to, or titrated with, the eluate from the Protein A antibody affinity chromatography, to obtain the treatment composition. The treatment composition then retains a pH range of 3.3 to 3.7 as it flows from the one unit operation to the next. The method does not rely on a pH meter or a pH feedback loop in controlling the function of a pump for starting, stopping, or otherwise adjusting rate of addition of the composition virus-inactivation reagent for combination with the eluate. Rather, pH of the treatment composition is maintained within an optimal range based on use of the single predetermined volumetric ratio. Since pH meters do not report pH in real time, eliminating the need for relying on a pH meter or a pH feedback loop improves the efficiency and accuracy of the viral inactivation step.

An understanding of main species of protein to be titrated with the addition of the composition including the virus-inactivating reagent is useful in predicting a priori the output of viral inactivation at low pH. Other variables that are useful include the effective total charge of the protein, the background buffer of the protein at the time of titration, the strength titrant (weak acid) and the ratio at which the protein A eluate and the virus inactivation reagent are mixed.

State of the art titration is automated as a batch or pool due to complexity involved with controlling a dynamic and changing system in a Protein A elution stream. A direct in-line titration, without a priori knowledge of the system, would require a thorough validation of one or more PID loops, pH probes, and pump metering. Such control is undesirable because pH probes are susceptible to response delays, drift, offsets, especially in a rapid-feedback environment.

Similar considerations apply regarding the method including use of a virus-inactivation reagent including a non-ionic detergent having a chromophoric group having an absorption peak between 230 nm and 600 nm.

Accordingly, in some examples, the composition including the virus-inactivation reagent has a pH that is determined by equation 1 and supporting equations 2 and 3:

$$\text{Viral Inactivation pH} = \text{Weak Acid } pKA + \text{Log}\left(\frac{M[\text{Sum of Base Species in System}]}{M[\text{Sum of Acid Species in System}]}\right) \quad \text{Equation 1}$$

$$\text{Sum of Base Species in System} = \left(Mab\frac{\text{mol}}{\text{kg}} * \text{effective } Mab \text{ Charge delta}\right) + \text{Conjugate Base Buffer Species} \quad \text{Equation 2}$$

$$\text{Viral Inactivation pH} = \text{Weak Acid } pKA + \\ \text{Log}\left\{\frac{M\left[\begin{array}{l}\text{Initial Weak Acid Conjugate Base} + \\ \left(Mab\frac{\text{mol}}{\text{kg}} * \text{effective } MabCharge \text{ delta}\right) + \\ \text{Background Buffer Conjugate Base}\end{array}\right]}{M\left[\begin{array}{l}\text{Initial Weak Acid Conjuage Acid} - \\ \left(Mab\frac{\text{mol}}{\text{kg}} * \text{effective } MabCharge \text{ delta}\right) - \\ \text{Background Buffer Conjuage Base}\end{array}\right]}\right\} \quad \text{Equation 3}$$

These examples may be considered to include use of a chemical control equation.

Also in some examples, a constant % v/v addition of the composition including the virus-inactivation reagent to the composition including the protein is banded within a pH range of a target pH with upper and lower bands of +/−0.1 pH. Here constant % v/v means combining the composition including the virus-inactivation reagent and the composition including the protein at a volumetric ratio that does not vary during the course of the combining, the volumetric ratio being provided as volume of the composition including the virus-inactivation reagent per volume of the composition including the protein, expressed as a percentage. In accordance with these examples, the upper band of the banded inactivation pH equals target pH+0.1 pH. The lower band of the banded inactivation pH equals pH of the composition including the virus-inactivation reagent, e.g. titrant.

Also in some examples, the % v/v addition of the composition including the virus-inactivation reagent is determined by equation 4 and supporting equations 5 to 9:

$$A = B/(C-B) \quad \text{Equation 4:}$$

A is the % v/v addition of the virus inactivation reagent
B is the final inactivating reagent molarity
C is the stock inactivating reagent molarity
Determining the final inactivating reagent molarity=sum of (final inactivating conjugate base molarity+final inactivating conjugate acid molarity).

$$B = \varepsilon(D+E) \quad \text{Equation 5:}$$

D=final inactivating conjugate base molarity
E=final inactivating conjugate acid molarity
Determining the final inactivating conjugate base molarity=total system conjugate base molarity−total system non reagent base molarities.

$$D = F-G \quad \text{Equation 6:}$$

F=total system conjugate base molarity
G=total system non reagent base molarities
Determining the final inactivating conjugate acid molarities=total system conjugate acid molarities−total system non reagent acid molarities.

$$E = H-G \quad \text{Equation 7:}$$

H=total system conjugate acid molarity
Determining the non-inactivating reagent base molarities is equal to the sum of background buffer conjugate base species and total charge molarity of the protein.

$$G = I+J \quad \text{Equation 8:}$$

I=background buffer molarity/$(1+(1/10^{\wedge}(pH_{ProAStream}-pKA_{backgroundbuffer})))$ J=Total charge molarity of the protein Determining the total protein charge at a given pH and molarity is the protein as molality multiplied by the total unblocked charges at inactivation pH.

J=protein concentration [g/L]/Molecular Weight
[MW]/(1-protein concentration[g/L]/1000×0.75)
*effective MAb Charge delta @inactivation pH     Equation 9

K=protein molality

Protein concentration is equal to the encountered concentration in a downstream unit operation. With Protein A streams, the concentration can be the result of several factors including Protein A loading challenge, strength of elution buffer (molarity &pH), flow rate of elution, product interaction with the Protein A matrix, and post elution level of dispersion and dilution.

L=total unblocked protein charges

L was predetermined from an internal library

The effective protein charges can be empirically determined by the methods described in "Effect of Protein and Solution Properties on the Donnan Effect During the Ultrafiltration of Proteins" Glen R. Bolton, Biotechnol. Prog., 2011, Vol. 27, No. 1, pages 140-152 (measurement of protein molecular charge, pages 145-146).

Wherein desired viral inactivation pH= $pKA_{viral\ inactivating\ reagent}$+log (total system conjugate base molarities/total system conjugate acid molarities)

$$M=N+Log(F/G)$$

M=Desired viral inactivation $pH_{operation\ temp}$
N=$pKA_{operation\ temp}$ of viral inactivating reagent
F=Total system conjugate base molarities
G=Total system conjugate acid molarities Also, in some examples, % v/v addition of the composition including the virus-inactivation reagent can be iteratively solved, for example by converging the value on the desired viral inactivation pH as a function of % addition of the selected virus-inactivation reagent, initial protein concentration, and predominant background buffer molarity.

As noted above, the single predetermined volumetric ratio has been selected to ensure that the predetermined property of the treatment composition is maintained across a range of concentrations predicted for the protein in the composition including the protein, without need for varying the volumetric ratio in response to variation in the concentration of the protein, and thus without need for using volumetric ratios other than the single predetermined volumetric ratio. The combining, at a single predetermined volumetric ratio, of the composition including the protein and the composition including the virus-inactivation reagent can include combining the compositions at volumetric ratios that vary slightly from that of the single predetermined volumetric ratio, e.g. based on varying from the single predetermined volumetric ratio by less, than or equal to 15%, less than or equal to 10%, less than or equal to 5%, and/or less than or equal to 1%, depending for example on variability associated with pumping of the composition including the protein and/or the composition including the virus-inactivation reagent during combination of these compositions to obtain the treatment composition.

Also in accordance with the method, steps (1) to (3) are carried out (a) continuously and (b) without feedback control being exerted by either adjustment of the volumetric ratio or diversion of the treatment composition.

Regarding steps (1) to (3) being carried out continuously, this means that step (1), step (2), and step (3) are carried out continuously, i.e. each step is carried out simultaneously, on different portions of the composition including the protein, the composition including the virus-inactivation reagent, and the treatment composition, for at least some period of time. For example, step (1), step (2), and step (3) can be carried out continuously for at least one hour, for at least 4 hours, for at least 12 hours, for at least 24 hours, for at least 3 days, for at least 10 days, or for at least 30 days, among other amounts of time. Also for example, step (4) can be carried out continuously with step (1), step (2), and step (3). Also for example, step (1), step (2), and step (3) can be carried out continuously, not just during overall manufacturing of the protein, but simultaneous to, and continuous with, actual production of the protein by a living system during manufacture of the protein.

Regarding steps (1) to (3) being carried out without feedback control being exerted by either adjustment of the volumetric ratio or diversion of the treatment composition, this means that steps (1) to (3) are carried out without correction of potential deviations of the treatment composition from the predetermined property for viral inactivation. Accordingly, steps (1) to (3) are carried out without feedback control being exerted by adjustment of the volumetric ratio at which the composition including the protein and the composition including the virus-inactivation reagent are combined. As noted above, the volumetric ratios may vary slightly from that of the single predetermined volumetric ratio, e.g. by less than or equal to 15%, less than or equal to 10%, less than or equal to 5%, or less than or equal to 1%, depending for example on variability associated with pumping, but not based on adjustment associated with feedback control. Also, steps (1) to (3) are carried out without feedback control being exerted by diversion of the treatment composition from a product stream, e.g. diversion away from a treatment vessel and/or a post-treatment processing operation. Steps (1) to (3) may be carried out with diversion of the treatment composition from a product stream for other reasons, e.g. due to intermittent sampling of protein, but not based on diversion associated with feedback control.

In some embodiments, the method also includes confirming that the treatment composition exhibits the predetermined property, e.g. for purposes of validation, though again not for feedback control. The confirming can be carried out by use of a detector, e.g. a pH meter, a conductivity meter, a temperature meter, a spectrophotometric device, or a spectroscopic device, that can be used to measure a characteristic of the treatment composition, e.g. pH, conductivity, temperature, a spectrophotometric characteristic, or a spectroscopic characteristic.

Considering the protein in more detail, the protein can be, for example, any of the proteins mentioned above, e.g. a therapeutic protein, such as an antibody, an antibody fragment, an antibody derivative, a cytokine, a growth factor, a hormone, an enzyme, or a blood coagulation factor, among others, or a vaccine protein, such as an antigenic protein, among others.

For example, the protein can be an antibody, antibody fragment, or antibody derivative. Also for example, the antibody, antibody fragment, or antibody derivative can be selected from the group consisting of an antibody, a monoclonal antibody, a polyclonal antibody, a mammalian antibody, a murine antibody, a primate antibody, a human antibody, a chimeric antibody, a primatized antibody, a humanized antibody, an immunoglobulin light chain, an immunoglobulin heavy chain, an immunoglobulin light chain and an immunoglobulin heavy chain, an antibody fragment, an antibody derivative, an Fab fragment, an F(ab')₂ fragment, an Fc fragment, an Fc-Fc fusion protein, an Fv fragment, a single chain Fv fragment, a single domain Fv fragment, a tetravalent single chain Fv fragment, a disulfide-linked Fv fragment, a diabody, a triabody, a tetrabody, a pentabody, a minibody, a miniantibody, an immunoglobulin single variable domain, an immunoglobulin single variable heavy domain, an immunoglobulin single variable light domain, a VHH domain, a humanized VHH domain, a single-domain antibody, a protein including an immunoglobulin single variable domain linked together in a modular format with another immunoglobulin single variable domain or a functional domain, a multivalent protein including two or more of the same immunoglobulin single variable domain linked together in a modular format, a biparatopic protein including two different immunoglobulin single variable domains linked together in a modular format, a bispecific protein including two different immunoglobulin single variable domains linked together in a modular format, a bi-functional protein including an immunoglobulin single variable domain and a functional domain linked together in a modular format, a domain-deleted antibody, a fusion polypeptide of an antibody fragment with another peptide or polypeptide, an Fc-peptide fusion, an Fc-toxin fusion, and a fusion of an antibody fragment and a scaffold protein.

As is well known in the art, antibodies are proteins that bind specifically to particular substrates, i.e. their antigens, with antibodies generally sharing a similar overall structure, i.e. an immunoglobulin structure, and with each particular antibody molecule having a unique structure that allows the particular antibody to bind specifically to its corresponding antigen. Exemplary antibodies are described, for example, by Murphy et al., Janeway's Immunobiology, 7th edition, Garland Science, New York (2008). As is also well known, an antibody can correspond to a monoclonal antibody or a polyclonal antibody, depending on how the antibody has been generated, can correspond to a mammalian antibody, a murine antibody, a primate antibody, or a human antibody, depending on the organism from the which the antibody was, or could have been, derived, can correspond to a chimeric antibody, a primatized antibody, or a humanized antibody, depending on whether the antibody has been modified toward making the antibody more suitable for use in a particular organism, and can correspond to an immunoglobulin light chain, an immunoglobulin heavy chain, or an immunoglobulin light chain and an immunoglobulin heavy chain, among others, depending on the structure of the antibody, as described, for example, by Tamashiro et al., Monoclonal Antibodies, pp. 409-433, in Animal Cell Technology: From Biopharmaceuticals to Gene Therapy (eds. Castilho et al.), Taylor & Francis Group, New York (2008), among others.

As is also well known, antibody fragments and antibody derivatives can be prepared from antibodies. For example, an Fab fragment (also termed fragment antigen-binding) consists of the variable regions of each of an immunoglobulin heavy chain and an immunoglobulin light chain, which are held together by adjacent constant regions. An Fab fragment may be formed by protease digestion, e.g. with papain, from conventional antibodies, or by genetic engineering. Similarly, an F(ab')₂ fragment includes the variable regions of each of two heavy chains and two light chains, also held together by adjacent constant regions. An F(ab')₂ fragment may be prepared by proteolytic cleavage by pepsin.

Moreover, using genetic engineering methods it is possible to produce a shortened antibody fragment that consists only of the variable regions of the heavy chain (VH) and of the light chain (VL), termed an Fv fragment (also termed fragment variable). Since an Fv fragment lacks constant regions of an immunoglobulin heavy chain and immunoglobulin light chain, and thus lacks covalent bonding between cysteines thereof, an Fv fragment often would be stabilized. For example, it is advantageous to use a short peptide to link the variable regions of the heavy chain and the light chain to stabilize an Fv fragment. The short peptide can include, for example, 10 to 30 amino acids, preferably 15 amino acids. In this way, a single peptide strand is obtained consisting of VH and VL, linked by a peptide linker. An antibody protein of this kind is known as a single-chain-Fv (also termed scFv). Exemplary scFv-antibody proteins of this kind are described by Huston et al., Proceedings of the National Academy of Sciences USA 85:5879-5883 (1988).

In addition, in recent years various strategies have been developed for preparing scFvs as a multimeric derivative. This is intended to lead, in particular, to recombinant antibodies having improved pharmacokinetic and biodistribution properties, as well as increased binding avidity. In order to achieve multimerization of scFvs, the scFvs were prepared as fusion proteins with multimerization domains. The multimerization domains may be, for example, the CH3 region of an immunoglobulin G (also termed IgG) or a coiled coil structure (helix structure) such as Leucine-zipper domains. There are also strategies in which the interaction between the VH/VL regions of the scFv are used for the multimerization, e.g. diabodies, triabodies, and pentabodies. among others.

Thus, for example, a diabody is a bivalent homodimeric scFv derivative. The shortening of the linker in an scFv molecule to 5 to 10 amino acids leads to the formation of homodimers in which an inter-chain VH/VL-superimposition takes place. Diabodies may additionally be stabilized by the incorporation of disulfide bridges. Exemplary diabodies are described, for example, by Perisic et al., Structure 2:1217-1226 (1994).

Also for example, a triabody is a trivalent homotrimeric scFv derivative. ScFv derivatives wherein VH-VL are fused directly without a linker sequence lead to the formation of trimers. Exemplary triabodies are described, for example, by Kortt et al., Protein Engineering 10:423-433 (1997).

Also for example, a minibody is a bivalent homodimeric scFv derivative. A minibody consists of a fusion protein which contains the CH3 region of an immunoglobulin, preferably IgG, most preferably IgG1, as the dimerization region that is connected to the scFv via a hinge region (e.g. also from IgG1) and a linker region. Exemplary minibody antibody proteins are described, for example, by Hu et al., Cancer Research 56:3055-3061 (1996).

Also for example, a miniantibody is an scFv derivative that has a bi-, tri-, or tetravalent structure. Miniantibody multimerization is carried out by di-, tri-, or tetrameric coiled coil structures, as disclosed for example by Lovejoy et al., Science 259:1288-1293 (1993), Pack et al., Biotechnology 11:1271-1277 (1993), and Pack et al., Journal of Molecular Biology 246:28-34 (1995).

Antibody fragments and antibody derivatives also include, for example, an immunoglobulin single variable domain. An immunoglobulin single variable domain can be, for example, an immunoglobulin single variable heavy domain (also termed VH domain) or an immunoglobulin single variable light domain (also termed VL domain), as described by Ward et al., Nature 341:544-546 (1989). An immunoglobulin single variable domain also can be, for example, a VHH domain, as derived from camelid heavy chain antibodies, as described by Hamers-Casterman et al., Nature 363:446-448 (1993), preferably a humanized VHH domain. An immunoglobulin single variable domain also can be, for example, a single-domain antibody. An immunoglobulin single variable domain also can be, for example, a NANOBODY(R) (trademark owned by Ablynx N.V.) therapeutic protein including one immunoglobulin single variable domain.

Antibody fragments and antibody derivatives also include, for example, a protein including an immunoglobulin single variable domain linked together in a modular format with another immunoglobulin single variable domain or a functional domain. Examples of such proteins include a multivalent protein including two or more of the same immunoglobulin single variable domain, e.g. two or more of the same VHH domain, linked together in a modular format, a biparatopic protein including two different immunoglobulin single variable domains, e.g. two different VHH domains, linked together in a modular format, each recognizing a different epitope on the same antigen, and a bispecific protein including two different immunoglobulin single variable domains, e.g. two different VHH domains, linked together in a modular format, each recognizing a different antigen. Examples of such proteins also include a bi-functional protein including an immunoglobulin single variable domain and a functional domain linked together in a modular format. Examples also include NANOBODY(R) multivalent, biparatopic, bispecific, and bi-functional therapeutic proteins.

Antibody fragments and antibody derivatives also include, for example, a fusion of an antibody fragment and a scaffold protein, i.e. a protein including an antibody fragment and a scaffold protein fused to form a single polypeptide chain. In this context, a scaffold protein can be any functional domain of another protein that has been coupled, e.g. by genetic cloning or by co-translational processes, with an antibody fragment.

Considering other types of proteins, the protein of interest also can be, for example, insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL, or G-CSF, GM-CSF, M-CSF, MCP-1 or VEGF. The protein of interest also can be, for example, erythropoietin or any other hormone growth factor. The protein of interest also can be, for example, a DARPin.

The protein can be made by a host cell. The host cell can be, for example, any of the cells mentioned above, e.g. a mammalian cell, a plant cell, or a bacterial cell, among others. The host cell can be, for example, a hamster cell, such as a BHK21, BHK TK⁻, CHO, CHO-K1, CHO-DUKX, CHO-DUKX B 1, or CHO-DG44 cell or a derivative/progeny of such a cell line. The host cell also can be, for example, a murine myeloma cell, e.g. an NSO and Sp2/0 cell or a derivative/progeny of such a cell line. The host cell also can be, for example, derivatives/progenies of those cells, other mammalian cells, including but not limited to human, mice, rat, monkey, and rodent cell lines, or other eukaryotic cells, including but not limited t yeast cells and insect cells. Exemplary host cells are described, for example, by Léo et al., Animal Cells: Basic Concepts, pp. 13-37, in Animal Cell Technology: From Biopharmaceuticals to Gene Therapy (eds. Castilho et al.), Taylor & Francis Group, New York (2008), among others.

The host cell can be cultivated in a culture medium. The culture medium can be, for example, a commercially available medium, such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-Invitrogen), serum-free CHO Medium (Sigma), and protein-free CHO Medium (Sigma). Any of the media may be supplemented as necessary with a variety of compounds, examples of which include hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations. Exemplary culture media are described, for example, by Moraes et al., Culture Media for Animal Cells, pp. 111-128, in Animal Cell Technology: From Biopharmaceuticals to Gene Therapy (eds. Castilho et al.), Taylor & Francis Group, New York (2008), among others.

The expression of the protein of interest by the host cell can include transcription and/or translation, within the host cell, of a nucleic acid sequence encoding the protein of interest. The level of expression of the protein of interest may be determined, for example, on the basis of the amount of corresponding mRNA encoding the protein of interest that is present in the host cell, the amount of the protein of interest present in the host cell, or the amount of the protein of interest secreted from the host cell, among other approaches. For example, the corresponding mRNA can be quantitated by Northern blot hybridization, ribonuclease RNA protection, in situ hybridization to cellular RNA, or RT-PCR, among other approaches, as described by Sambrook et al., Molecular Cloning: A Laboratory Manual, 2d edition, New York, Cold Spring Laboratory Press (1989), and Ausubel et al., Current Protocols in Molecular Biology, (1987-2014), among others. Also for example, the amount of the protein of interest, as present in the host cell or as secreted therefrom, can be quantitated by various methods, e.g. by ELISA, by Western blotting, by radioimmunoassay, by immunoprecipitation, by assaying for the biological activity of the protein, by immunostaining of the protein followed by FACS analysis, or by homogeneous time-resolved fluorescence (HTRF) assays, among other approaches, again as described by Sambrook et al. (1989), and Ausubel et al. (1987-2014), among others.

Cultivation of a host cell in a culture medium, with expression of the protein by the host cell, can be carried out by any of the processes for producing a protein mentioned above, for example a homogeneous process, e.g. suspension culture based on use of a stirred-tank bioreactor, air-lift bioreactor, or wave bioreactor, or a heterogeneous process, e.g. adherent culture based on a microcarrier-based system, a packed bed bioreactor, or a hollow-fiber bioreactor, as carried out in a discontinuous mode, e.g. batch cultivation or fed-batch cultivation, or in a continuous mode, e.g. continuous cultivation with perfusion, and as carried out at any suitable scale, e.g. laboratory, pilot, or production scale. Exemplary processes are described, for example, by Véliz et al., Bioreactors for Animal Cells, pp. 221-258, in Animal Cell Technology: From Biopharmaceuticals to Gene.

The protein in the composition including the protein may be present at various concentrations. For example, the concentration of the protein in the composition including the protein can be 10 to 70 mg/mL. Also for example, the concentration of the protein in the composition including the protein can be 20 to 65 mg/mL, 30 to 60 mg/mL, 40 to 55 mg/mL, and/or about 50 mg/mL.

A protein made according to the method for continuously inactivating a virus during manufacture of a protein is also provided. The protein can be a protein as described above.

Figure 4:
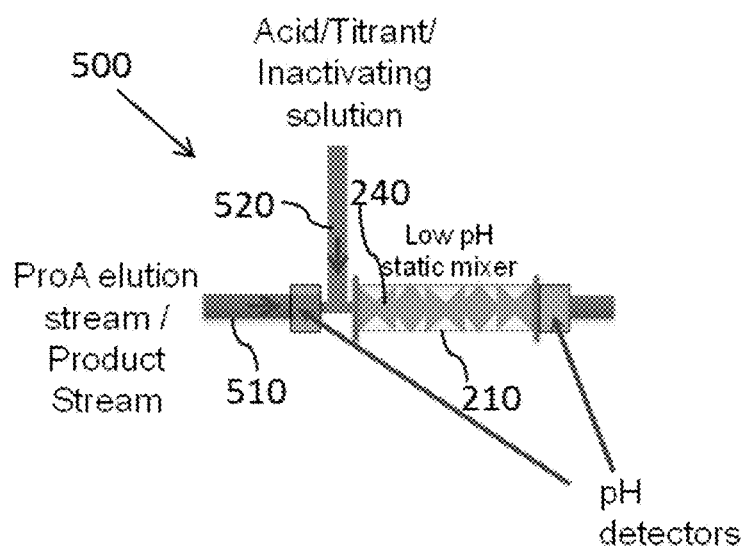
FIG. 4 is a schematic view of an exemplary system 500 for carrying out the method for continuously inactivating a virus during manufacture of a protein.

An exemplary system 500 for carrying out the method for continuously inactivating a virus during manufacture of a protein is shown in FIG. 4, which illustrates a viral inactivation flow path for chemical control. The exemplary system 500 includes (i) a protein stream input 510, e.g. a Protein A elution stream and/or a product stream input, (ii) a virus-inactivating reagent solution input 520, e.g. an acid/titrant/inactivating solution input, and a treatment vessel 210 including a static mixer 240, e.g. a low pH static mixer. The method can be carried out using the exemplary system 500 as discussed above. In accordance with the method, pre-determined rate/% addition of a viral titrant is added to the main product flow to tightly control pH and inactivation. In accordance with the exemplary system 500, pH detectors are used to measure the process, but not to control the process. Accordingly, the pH detectors are merely used for monitoring pH, not for controlling the amount or the timing of acid addition to the exemplary system 500.

Advantages of the method for continuously inactivating a virus during manufacture of a protein, as provided, include the following: (1) Provide continuous viral inactivation at a tight pH range of 3.3 to 3.7, for example pH 3.4 to 3.6, which is the optimal pH range for virus inactivation; (2) Predetermine the % virus inactivating reagent by a mathematical formula; (3) Avoid dynamic control of pH and concentration adjustments by constant volume additions; (4) Inactivate continuous or periodic process streams; (5) Eliminate static process holds and associated break tanks in the continuous and periodic stages; (6) Automate stream inactivation and immediately begin viral inactivation; (7) Handle inactivation with dynamic stream and solution concentrations and pH; (8) Inactivate any process flow rate; (9) Automatically match inactivation to process flow rate; (10) Inactivate Protein A elution streams; (11) Avoid over-titration of inactivation and preserve product quality; (12) Use any configuration of a continuous low pH viral inactivation system by placement of the inactivation stage in the periodic section of the system; (13) Use the same approach for base addition, e.g. after inactivation of virus at low pH and before a further processing operation of anion exchange chromatography (thus corresponding to titration, rather than inactivation); (14) Achieve the desired conditions for the next unit operation; (15) Use the same approach for detergent inactivation; and (16) Minimize cost, complexity, time, and facility size for manufacturing monoclonal antibodies.

A method for inactivating one or more viruses in a sample also is provided. The method includes continuously mixing the sample with one or more virus-inactivating reagents as the sample flows from a first unit operation to a second unit operation during a process for purifying a target molecule. In accordance with the method, the ratio of the one or more virus-inactivating reagents to the sample is determined independently of, or without, a feedback control mechanism.

The method for inactivating one or more viruses in a sample can be carried out in accordance with the principles and approaches discussed above. For example, the sample can correspond to a composition including a protein, as discussed above. Also for example, the one or more virus-inactivating reagents can be provided in a composition including the virus-inactivating reagents, as discussed above. Also for example, the first unit operation can be a pre-treatment processing step, as discussed above. Also for example, the second unit operation can be a post-treatment processing step, as discussed above. Also for example, the ratio of the one or more virus-inactivating reagents to the sample can be determined in advance, and thus predetermined, as discussed above. Also for example, the ratio of the one or more virus-inactivating reagents to the sample can be determined independently of, or without, a feedback control mechanism, such as a pH control feedback loop, as discussed above.

In accordance with this method, the ratio of the one or more virus inactivating reagents to the sample can be determined, as discussed above, as % v/v by equation 1 and supporting equations 2 and 3:

$$\text{Viral Inactivation pH} = \text{Weak Acid } pKA + \text{Log}\left(\frac{M[\text{Sum of Base Species in System}]}{M[\text{Sum of Acid Species in System}]}\right) \quad \text{Equation 1}$$

$$\text{Sum of Base Species in System} = \left(Mab\frac{\text{mol}}{\text{kg}} * \text{effective } Mab \text{ Charge delta}\right) + \text{Conjugate Base Buffer Species} \quad \text{Equation 2}$$

$$\text{Viral Inactivation pH} = \text{Weak Acid } pKA + \text{Log}\left(\frac{M\left[\text{Initial Weak Acid Conjugate Base} + \left(Mab\frac{\text{mol}}{\text{kg}} * \text{effective } MabCharge \text{ delta}\right) + \text{Background Buffer Conjugate Base}\right]}{M\left[\text{Initial Weak Acid Conjuage Acid} - \left(Mab\frac{\text{mol}}{\text{kg}} * \text{effective } MabCharge \text{ delta}\right) - \text{Background Buffer Conjuage Base}\right]}\right) \quad \text{Equation 3}$$

A protein made according to the method for inactivating one or more viruses in a sample is also provided. The protein can be a protein as described above.

Advantages of the method for inactivating one or more viruses in a sample, as provided, are like those of the method for continuously inactivating a virus during manufacture of a protein, as discussed above.

EXAMPLES

Example 1

Integrated bioprocessing may provide advantages with respect to more flexible and manageable clinical manufacturing. Continuous/integrated processing can add robustness and reduce cost, through, for example, increased automation, reduced equipment size, and increased resin utilization.

An exemplary continuous manufacturing process involves (i) perfusion reactor and harvest, (ii) continuous protein A capture (e.g. involving two or more columns), (iii) continuous low pH viral inactivation, and (iv) polishing column chromatography (e.g. anion exchange chromatography). Low pH viral inactivation is critical for this process.

In this context, a chemical control concept for continuous inactivation of virus is disclosed here. A goal is to develop a single titrant solution at a single ratio to maintain a tight low pH window over an entire elution. This would rely on pump-level robustness, rather than PID feedback loops governed by pH response. A key factor would be to determine a suitable titrant to use as a virus-inactivation reagent, and more particularly a % v/v at which the titrant can be added to the elution, a suitable concentration for the titrant, and a suitable pH for the titrant, in order to obtain an output for inactivation of virus corresponding to pH 3.4 to 3.6.

Current industry practice relies on batch Protein A elution and pool inactivation. In a batch process, one column volume to several or more column volumes of material is pooled from an elution into a container. The pool is manually titrated with a weak acid to achieve a low pH and thus to initiate viral inactivation. State-of the art low pH inactivation is conducted with automated titrations. This can include, for example, pooling Protein A elutions, to obtain a Protein A elution pool including a protein at, for example, 12 to 15 g/L at pH 3.8 to 4.0, then titrating the pool with weak acid at 1-10% to achieve a pH of 3.5.

Figure 5:
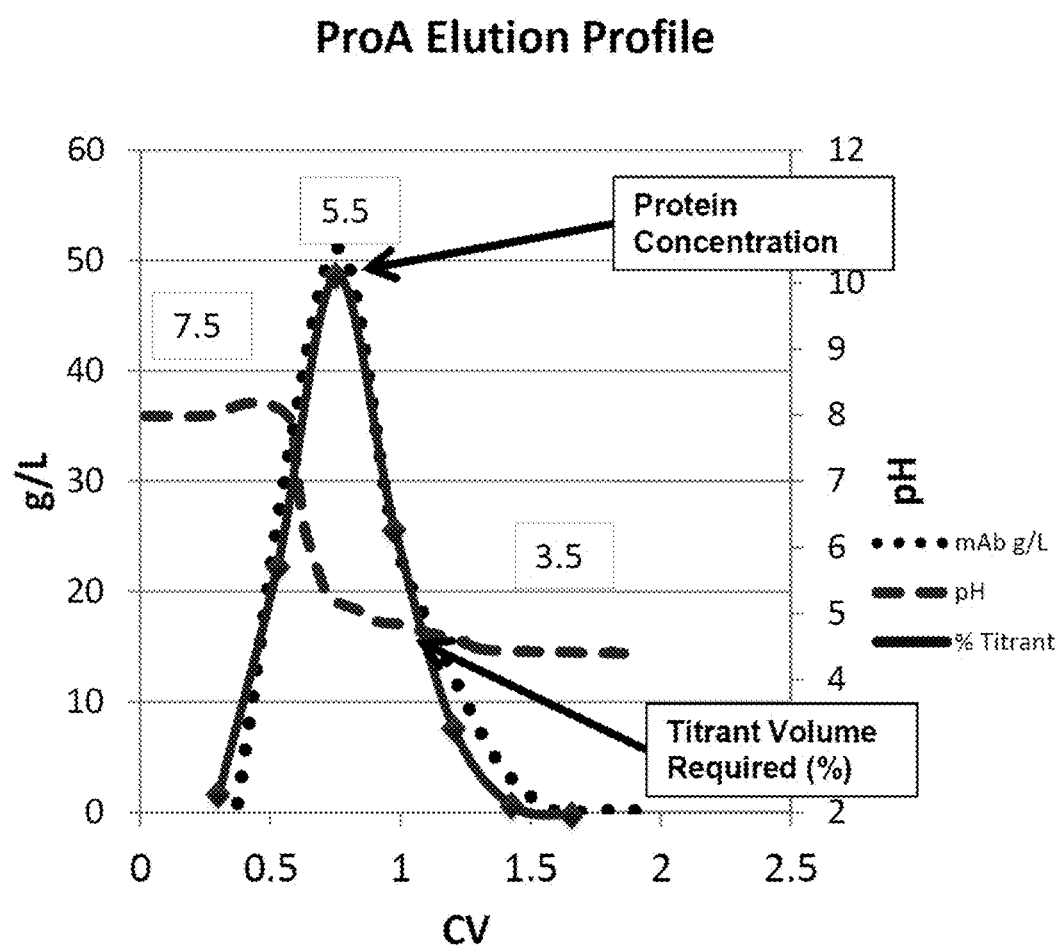
FIG. 5 is a Protein A elution profile that shows results for batch titration of a Protein A elution, in which the solid green line corresponds to concentration of monoclonal antibody (g/L per column volume), the solid red line corresponds to pH of the Protein A elution (per column volume), and the solid blue line corresponds to relative titrant volume required to obtain a treatment composition having pH 3.5 (per column volume)

To test the chemical control concept, fraction titrant requirements were determined, based on off-line fractionation. Interestingly, although Protein A elutions decrease in pH from about pH 7.5 to about pH 4.5 over the course of elution, fractions of Protein A elutions having the highest pH, i.e. about pH 7.5, did not result in the highest need for titrant to achieve a lower pH. Rather, surprisingly, the need for titrant was driven by the concentration of protein in the fractions of Protein A elutions. This is shown in FIG. 5, which illustrates that the percent titrant needed was strongly correlated with protein concentration.

Based on these results, key factors for a model emerged. The key factors include protein variables, including peak protein concentration during elution (or prior to titration), and protein charge. The key factors also include titrant variables, including min/max pH for monoclonal antibody stability and viral clearance, and min/max % additions for mixing and dilution impact. Other considerations include chromatography buffers and flow rate impact, though these are constants with respect to a given platform. Other considerations also include anionic considerations with respect to polishing by anion exchange chromatography.

In considering peak impact as buffer equivalents, the model predicts that protein and charge at peak protein elution are greater than or equal to 100 mM buffer. The wash buffer corresponds to 10 mM buffer.

Considering worst-case peak concentrations within constraints, under current constraints the elution max peak concentration was about 50 g/L. This is based on two monoclonal antibodies, as discussed in more detail below, corresponding to 48 to 58 g/L (10% dynamic binding capacity). Elution buffers were held constant with respect to the platform. Concentrations were determined in line, based on Flow VPE Kinetic used with initial 0.1 mm pathlength and 100+Au/cm linearity.

A spectrum of charge densities were identified for various proteins. Interestingly, as shown in TABLE 1, charge densities were relatively clustered for monoclonal antibodies, in contrast to other proteins.

TABLE 1

Relative clustering of charge densities of monoclonal antibodies.

| Molecule | Total Charges at pH 3.5 |
|---|---|
| MAb1 | 140 |
| MAb2 | 139 |
| MAb3 | 133 |
| MAb4 | 126 |
| MAb5 | 119 |

The results suggest that universal titrant conditions may be possible for continuous inactivation of virus in processes for manufacturing monoclonal antibodies.

A chemical control equation was developed. In accordance with the equation, conditions for viral inactivation pH can be determined using the Henderson-Hasselbalch equation for weak acid, with (MAb(mol/kg)*effective MAb Charge delta) as base titrant.

In line commands include the following:

Protein A elution flow rate+constant % addition of titrant=banded inactivation pH.

In accordance with this approach, the upper band of pH for inactivation of virus equal target pH+0.1 pH. The lower band equals titrant pH.

Figure 6:
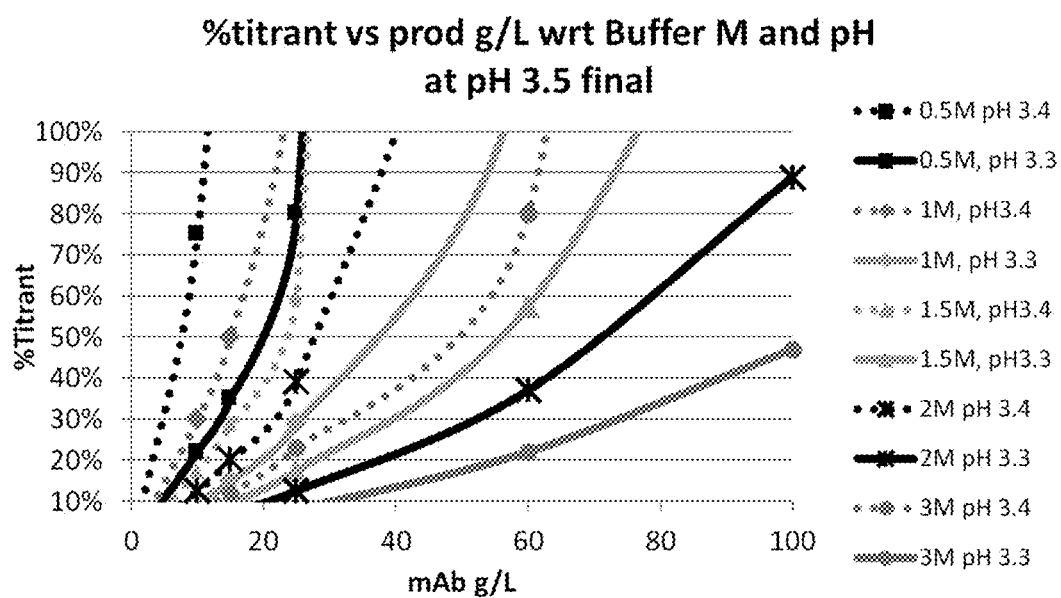
FIG. 6 is a plot of volume of titrant required to achieve pH 3.5 upon combination with Protein A eluate (expressed as % volume titrant solution/volume eluate, meaning volume of titrant solution per volume of Protein A eluate, expressed as a percentage) versus concentration of monoclonal antibody in the Protein A eluate (g/L), for titrant solutions corresponding to 2 M glycine at pH 3.3, 2 M glycine at pH 3.4, 1.5 M glycine at pH 3.3, 1.5 M glycine at pH 3.4, 1 M glycine at pH 3.4, 1 M glycine at pH 3.3, 0.5 M glycine at pH 3.4, 0.5 M glycine at pH 3.3, 3 M glycine at pH 3.4, and 3 M glycine at pH 3.3 (ordered as in legend, from top to bottom)

Model data for an operation window were generated, with respect to % conditioning, product g/L, titrant molarity, and titrant pH, for an exemplary monoclonal antibody, MAb2. Results for various titrant solutions are shown in FIG. 6. Flat curves throughout the space are ideal. As can be seen, few combinations solve for pH 3.5 at a concentration of monoclonal antibody of 50 g/L.

Figure 7:
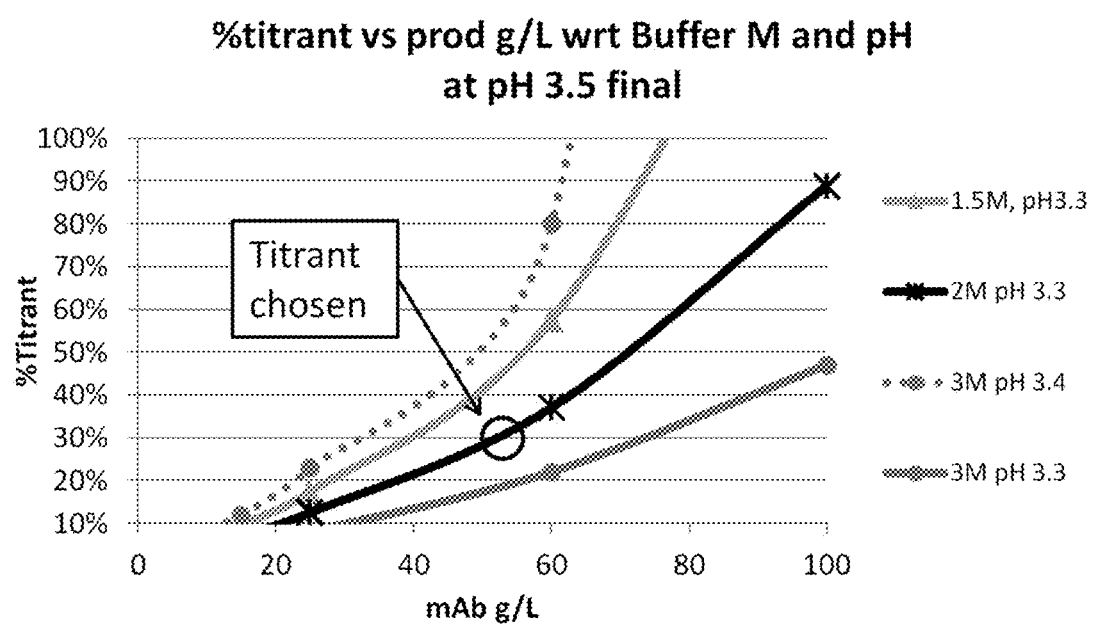
FIG. 7 is a plot of volume of titrant required to achieve pH 3.5 upon combination with Protein A eluate (again expressed as % volume titrant solution/volume eluate) versus concentration of monoclonal antibody in the Protein A eluate (g/L), for titrant solutions corresponding to 3 M glycine at pH 3.4 (line with short line symbol), 1.5 M glycine at pH 3.3 (line with triangle), 2 M glycine at pH 3.3 (upper line with diamond, corresponding to titrant chosen), and 3 M glycine at pH 3.3 (lower line with diamond)

A subset of the titrant solutions were considered for further testing. Results for the subset of the titrant solutions are shown in FIG. 7. A lead titrant solution, corresponding to 2 M glycine at pH 3.3, and thus corresponding to 0.2 units below the target pH of 3.5, was chosen. Of note, as can be seen from FIG. 7, a titrant solution of 3M glycine at pH 3.3 also would be suitable. Interestingly, though, although the titrant solution of 3 M glycine at pH 3.3 would seem to be better based on theoretical considerations, given that it can be used to solve for pH 3.5 at a concentration of monoclonal antibody of 50 g/L based on a lower addition volume than for the titrant solution of 2 M glycine at pH 3.3, surprisingly it was observed that the titrant solution of 2 M glycine at pH 3.3 provides an advantage relative to the titrant solution of 3 M glycine at pH 3.3 in terms of more precise control of pH and titrant concentration during addition thereof, and thus lower risk of unwanted side effects to protein, and corresponding greater flexibility in use of the system. Accordingly, as can be seen, the lead titrant solution of 2 M glycine at pH 3.3 resulted in a well-matched addition volume of 33% (expressed as % volume titrant solution/volume eluate, meaning volume of titrant solution per volume of Protein A eluate, expressed as a percentage).

Monoclonal antibody charge impact of selected titrants was determined, as shown in TABLE 2.

TABLE 2

Monoclonal antibody charge impact on selected titrant.

| Molecule | Total Charges at pH 3.5 | Model % Titrant [50 g/L, pH 3.5] | Actual % Titrant [50 g/L, pH 3.5] |
|---|---|---|---|
| MAb1 | 140 | 33.6% | Not determined |
| MAb2 | 139 | 33.5% | 32% |

TABLE 2-continued

Monoclonal antibody charge impact on selected titrant.

| Molecule | Total Charges at pH 3.5 | Model % Titrant [50 g/L, pH 3.5] | Actual % Titrant [50 g/L, pH 3.5] |
|---|---|---|---|
| MAb3 | 133 | 31.3% | Not determined |
| MAb4 | 126 | 29.4% | 28% |
| MAb5 | 119 | 27.1 | Not determined |

The results suggest that the spread of monoclonal antibodies can be solved with addition volumes of the lead titrant of 27-34% (again expressed as % volume titrant solution/volume eluate). As can be seen, direct titrations support model outputs. The results suggest that a universal titrant may be possible. This may allow for simplicity and robustness in place of volumetric inefficiencies associated with current industry practices.

Figure 8:
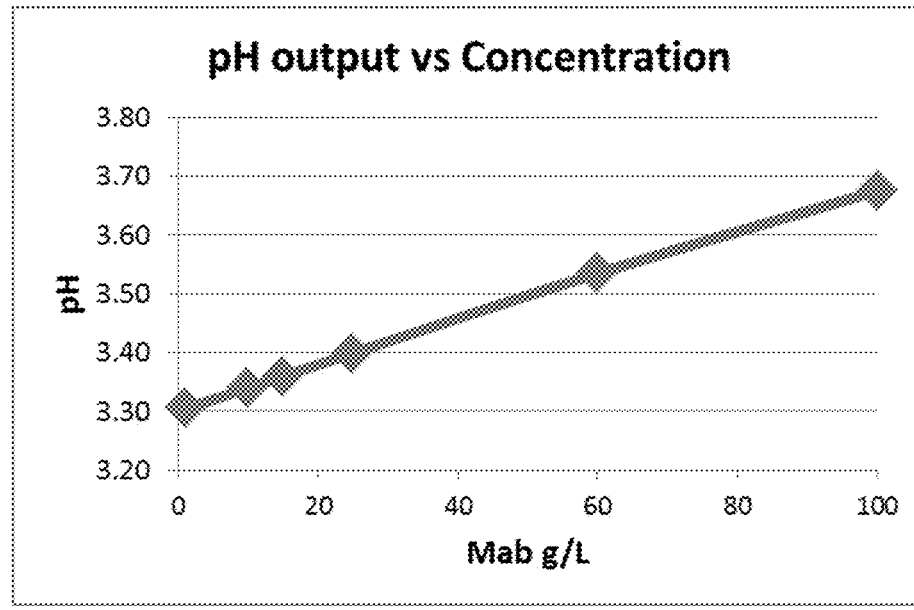
FIG. 8 is a plot showing results of excursion testing for monoclonal antibody, expressed as pH output versus concentration of monoclonal antibody (g/L)
Figure 9:
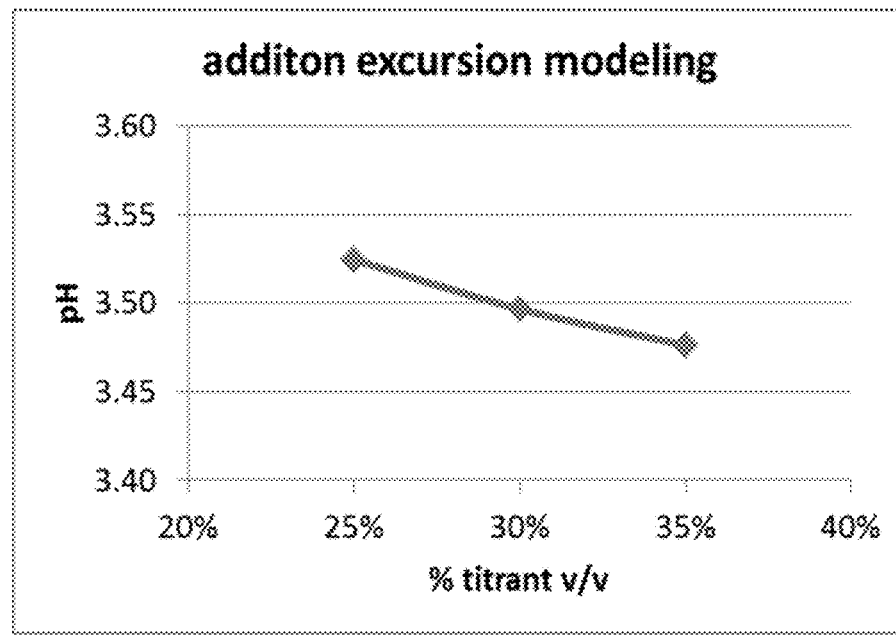
FIG. 9 is a plot of results of excursion testing for titrant, expressed as output pH versus titrant volume (again expressed as % volume titrant solution/volume eluate)

Robustness of this approach to excursions was also tested. As shown in FIG. 8, excursion of monoclonal antibody to a higher concentration of 60 g/L resulted in an increase in pH of only 0.03 units. Moreover, excursion of monoclonal antibody to lower concentrations resulted in a decrease in pH to that of lead titrant, i.e. pH 3.3. Also, as shown in FIG. 9, relative addition excursions of 15% with respect to the addition volume % of lead titrant (e.g. modeling pump excursions), resulted in a change of pH of 0.02 units.

These results and other are considered in more detail in the examples in the examples that follow.

Example 2

General Conditions for Low pH Continuous Virus Inactivation.

In order to enable low pH continuous virus inactivation for a continuous process, product corresponding to eluate from a Protein A chromatography column is mixed in-line with a virus-inactivating reagent corresponding to an acid (e.g. 1.5 to 3 M glycine or acetic acid) using a three-way valve and passed through a static mixer. The static mixer dimensions are chosen so as to enable efficient mixing of the acid and product streams. In order to provide sufficient residence time for robust virus inactivation, which can be for example 60 min, but which also can be for example as a short as 1 to 5 min, a tube of sufficient volume may follow after the static mixer. To end the virus inactivation, the virus inactivated stream is mixed with base (e.g. 1 to 2 M HEPES pH 8.0 or Tris-base at pH 11) using a three-way valve and passed through a static mixer to enable mixing and to increase the pH to a pH that is suitable for the next purification step in the continuous process, e.g. typically pH 5 to 8.1.

Example 3

In this experiment, a monoclonal antibody designated MAbD was diafiltered into a neutral pH solution or Protein A wash solution preceding the elution and manually titrated with the viral inactivating solution. The goal of the experiment was to quantitate how accurately the model predicted the % titrant needs at different protein concentrations.

The MAbD used in these studies was a purified humanized IgG2 produced in Chinese hamster ovary cells grown in chemically defined medium. The protein was assigned a molecular weight of 150,000 Daltons. A theoretical isoelectric point was determined from amino acid sequence, and an actual isoelectric point of was determined from an isoelectric focusing gel. The material used was either Protein A load material or purified pre-formulation material.

Protein concentrations were measured using a UV spectrophotometer statically with SoloVPE, C Technologies integrated with a Cary 50 Bio, Varian Instruments and in-line with a FlowVPE, C Technologies integrated with a Cary 50 Bio, Varian Instruments. The extinction coefficient used for calculation of protein concentration from UV absorbance was predicted from theory.

The protein pH was measured statically with a Thermo/Orion 4-Star pH meter with active temperature compensation. The pH probe was Orion 8102BNUWP ROSS Ultra pH Electrode measured at room temperature 22±3° C.

The Protein A elution buffers in the system consist of either acetate or glycine, which does not have impactful temperature coefficient pH offsets in the measured samples. The low pH inactivating reagents consist of either acetate or glycine, which also does not have impactful temperature coefficient pH offsets in the measured samples.

Measurement variability could arise from pre-elution Protein A wash solutions which could consist of either Tris or Phosphate. Additionally, the protein structure and titratable amino acids could demonstrate temperature-dependent offsets.

The Protein A purification was performed on an AKTA Explorer 100 system and the pH trended with the integral probes. The molecules were loaded on new low cycle number resin to 10% dynamic binding capacity (also termed DBC) at variable flow rates between 60 and 240 cm/hr. The Protein A matrix used was either Mab Select matrix or Mab Select Sure LX matrix. The column heights were between 19 and 26 cm. The loaded column was washed with one or more wash solutions to reduce non-specific binding and place the column in a solution with low titration needs. The elution was performed with either 25 mM Sodium Acetate pH 3.5 or 150 mM Glycine pH 3.5 at 60-240 cm/hr.

An exemplary pilot scale protocol for the Protein A purification is as follows. For load material, titer corresponded to 3.2 mg/mL. The column was loaded to 40 mg/mL. Flow rates and volumes are provided in TABLE 3. During the Protein A stream elution, an additional flow rate was added via an AKTA cVI Explorer system. The % titrant addition was 30% (again expressed as % volume titrant solution/volume eluate). The Pump A flow rate for elution stream addition was 18.25 mL/min.

TABLE 3

Flow rates and volumes for AKTA Explorer 100 system pilot Protein A purification.

| Process Step | Components | Column Volume (#) | Volume (mL) | Flow Rate (mL/min) | Linear Flow Rate (cm/hr) | Tare Weight/ Fraction (grams)/ (#) | Full Weight/ Fraction (grams)/ (#) | Final Weight (grams) |
|---|---|---|---|---|---|---|---|---|
| Equilibration | 50 mM Tris, 150 mM NaCl, pH 7.5 | 5 | 1901 | 76.0 | 300.0 | NA | NA | NA |
| Load | | n/a | 618 | 60.8 | 240.0 | 205 | 1454 | 1249 |
| Wash | 50 mM Tris, 150 mM NaCl, pH 7.5 | 2 | 760 | 0.0 | | | | |
| Wash 2 | 0.5M CaCl2, 50 mM Tris, pH 7.5 | 5 | 1901 | 76.0 | 300.0 | 42 | 162 | 120 |
| Wash 3 | 10 mM Tris, 10 mM NaCl, pH 7.5 | 3 | 1140 | 76.0 | 300.0 | 42 | 113 | 71 |
| Prepeak Elution | 25 mM Acetate, pH 3.5 | 0.50 | 36 | 60.8 | 240.0 | 42 | 62 | 20 |
| Peak | 25 mM Acetate, pH 3.5 | 3 | 1140 | 60.8 | 240.0 | 42 | 112 | 70 |
| Strip | 50 mM Glycine, 250 mM NaCl, pH 2.7 | 5 | 1901 | 76.0 | 300.0 | 42 | 159 | 117 |
| Regen | 50 mM NaOH, 0.5M Sodium Sulfate | 5 | 1901 | 76.0 | 300.0 | NA | NA | NA |
| Storage | 16% Ethanol, 50 mM Tris, 150 mM NaCl, pH 7.5 | 4 | 1521 | 76.0 | 300.0 | NA | NA | NA |

Material for static titration measurements was taken from the Protein A purification, described above, as a pool, neutralized to pH 7.5±0.2, and further diafiltered and concentrated via ultrafiltration/diafiltration (also termed UF/DF). The material was diafiltered for 7 or more "diavolumes" against 10 mM Tris, 10 mM NaCl pH 7.5, the final Protein A wash buffer. A final concentration step was performed to recover the material at >75 g/L as measured by the SoloVPE. The material measured pH 7.5±0.1 indicating no pH offset occurred as a result of concentration or buffer.

The UF/DF system used was manually assembled using a Quattro flow diaphragm pump, Biopharm tubing, and a 30 kD Millipore PLCTK composite regenerated cellulose membrane.

For piloting and demonstration purposes, the inline low pH viral inactivation was performed with a dedicated AKTA Explorer 100 system, named the cVI Explorer, separate from the Protein A AKTA Explorer system. The system was re-piped to accept a main protein flow from the Protein A Explorer system via the injection valve and add a flow (inactivating reagent) via Pump A directly into the mixing chamber or a T and static mixer. The resulting mixed solution was trended for pH with the in-line AKTA probe. The cVI Explorer system was programed to load the inactivation flow path with the inactivating reagent. Upon detection of a UV signal it directed the Protein A stream from waste to in-line for inactivation. The Pump A was set such that the flow from Pump A would be equal to the % v/v addition pre-determined for the inactivation and set in relation to the Protein A stream flow rate. For example if the determination for inactivation was a 30% v/v addition of the virus-inactivation reagent, then if the Protein A stream were coming in at 50 ml/min, the cVI Explorer system would be programed to have Pump A deliver 15 ml/min of inactivating reagent into the stream.

The static measurements of low pH viral inactivation were performed with the previously described diafiltered material with known background buffer composition. Solutions measuring 75 g/l through 0 g/L were titrated with inactivating reagents stepwise to achieve pH 3.50 at 22 ±3° C. and measured with previously described pH meter and probe.

Results are provided in TABLE 4.

TABLE 4

Predictive and actual titration of MAbD.

| Molecule: MAbD Initial Concentration (g/L) | Model pH 3.50 at 25° C. 2M Glycine pH 3.3 | Actual pH 3.5 at 21-23° C. 2M Glycine pH 3.3 |
|---|---|---|
| 75 | 35.0% | 34.0% |
| 50 | 24.1% | 21.3% |
| 25 | 13.5% | 12.0% |
| 10 | 7.1% | 5.7% |
| 1 | 3.4% | 2.0% |
| 0 | 3.0% | 2.0% |

Example 4

In this experiment, a monoclonal antibody designated MAbB was diafiltered into a neutral pH solution or Protein A wash solution preceding the elution and manually titrated with the viral inactivating solution. The goal of the experiment was to quantitate how accurately the model predicted the % titrant needs at different protein concentrations.

The MAbB used in these studies was a purified humanized IgG1 produced in Chinese hamster ovary cells grown in chemically defined medium. The protein was assigned a molecular weight of 150,000 Daltons. A theoretical isoelectric point was determined from amino acid sequence, and an actual isoelectric point of was determined from an isoelectric focusing gel. The material used was Protein A purified material.

The studies were carried out as described above.

Results are provided in TABLE 5.

TABLE 5

Predictive and actual titration of MAbB.

| Molecule: Bap Initial Concentration (g/L) | Model pH 3.50 at 25° C. 2M Glycine pH 3.3 | Actual pH 3.5 at 21-23° C. 2M Glycine pH 3.3 |
|---|---|---|
| 75 | 51.7% | 52% |
| 50 | 34.6% | 30% |
| 25 | 18.8% | 17% |
| 10 | 9.3% | 6% |
| 1 | 3.6% | 3% |
| 0 | 3.0% | 2% |

Example 5

In this experiment, MAbD was continuously inactivated in-line with a preset % volume addition of a predetermined viral inactivation solution, including Glycine. The run was at a 100 L reactor scale, operated in multiple column continuous Protein A capture, where the periodic elutions were inactivated with the chemical control concept.

Figure 10:
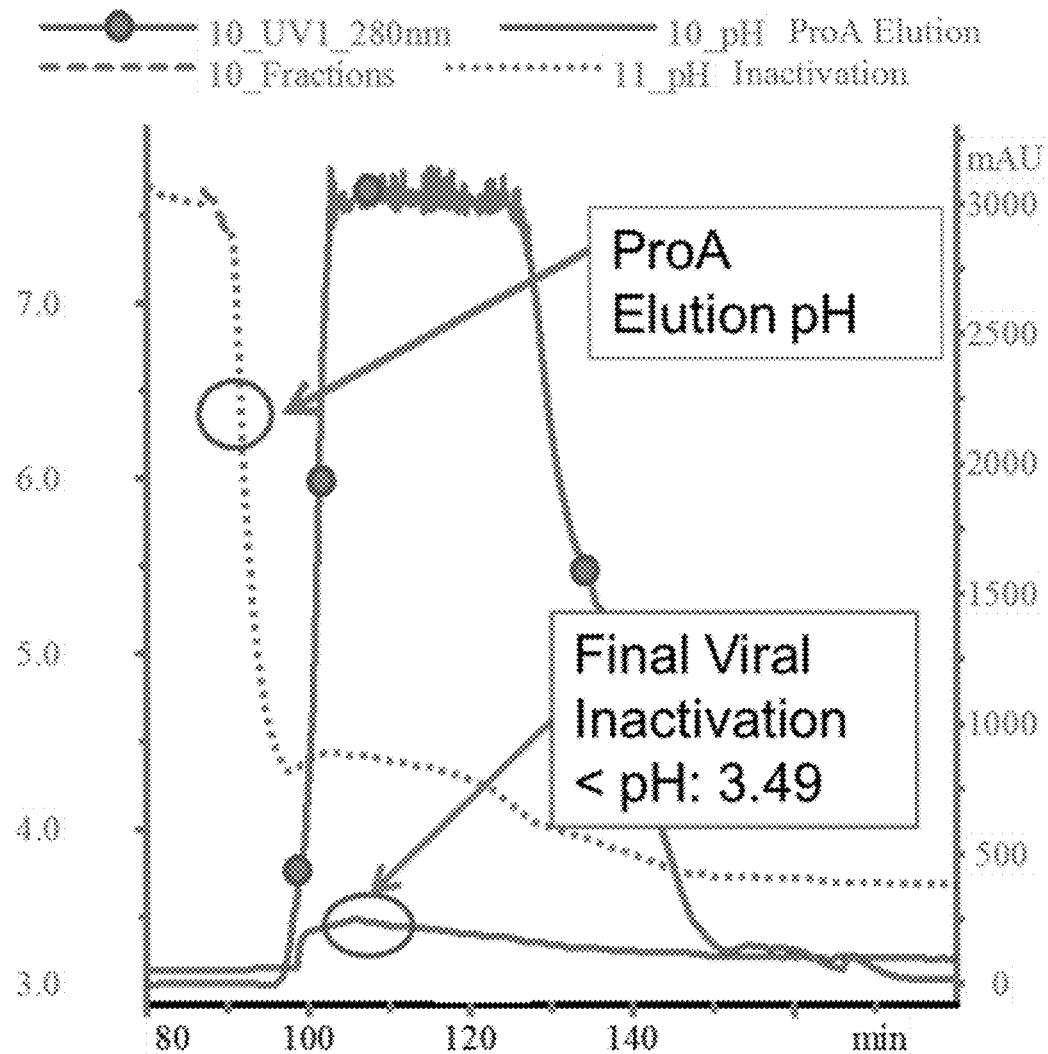
FIG. 10 is a Protein A elution profile that shows results for a 100 L reactor in-line with Protein A and continuous low pH viral inactivation, in which the solid blue line corresponds to relative concentration of monoclonal antibody in the Protein A elution, measured as mAU at 280 nm (per time), the dotted red line corresponds to pH of the Protein A elution (per time), and the solid red line corresponds to pH of the final viral inactivation treatment composition (per time).

Results are shown in FIG. 10. The results indicate achievement and maintenance of an output pH within specifications for continuous viral inactivation with respect to a dynamic Protein A stream. The results were achieved with one solution of virus-inactivation reagent, at one dilution, without under-shooting pH, thus demonstrating stability.

Together the results of these examples indicate that chemical control of low pH viral inactivation can be robustly achieved a priori. This can be accomplished through knowledge of maximal charges needed for titration. The volumetric ratio of titrant to mobile phase achieves pH targets without over-titration. Accordingly, pH measurement can be reduced to affirmation trending rather than active control.

It will be apparent to those skilled in the art that various modifications and variations can be made to the described embodiments without departing from the spirit and scope of the claimed methods. Thus, it is intended that present claimed methods cover the modifications and variations of the embodiments described herein provided that they come within the scope of the appended claims and their equivalents.

INDUSTRIAL APPLICABILITY

The methods disclosed herein are useful for continuously inactivating a virus during manufacture of protein, and thus for improving industrial methods for manufacturing proteins.

The invention claimed is:

1. A method for inactivating one or more viruses in a sample, wherein the method comprises continuously mixing the sample with one or more virus inactivating reagents as the sample flows from a first unit operation to a second unit operation during a process for purifying a target molecule, wherein the ratio of the one or more virus inactivating reagents to the sample is determined independently of, or without, a feedback control mechanism, wherein the ratio of the one or more virus inactivating reagents to the sample is determined as % v/v by equation 1 and supporting equations 2 and 3:

$$\text{Viral Inactivation pH} = \text{Weak Acid } pKA + \text{Log}\left(\frac{M[\text{Sum of Base Species in System}]}{M[\text{Sum of Acid Species in System}]}\right) \quad \text{Equation 1}$$

$$\text{Sum of Base Species in System} = \left(Mab\frac{\text{mol}}{\text{kg}} * \text{effective } Mab \text{ Charge delta}\right) + \text{Conjugate Base Buffer Species} \quad \text{Equation 2}$$

$$\text{Viral Inactivation pH} = \text{Weak Acid } pKA + \text{Log}\left(\frac{M\left[\text{Initial Weak Acid Conjugate Base} + \left(Mab\frac{\text{mol}}{\text{kg}} * \text{effective } MabCharge \text{ delta}\right) + \text{Background Buffer Conjugate Base}\right]}{M\left[\text{Initial Weak Acid Conjuage Acid} - \left(Mab\frac{\text{mol}}{\text{kg}} * \text{effective } MabCharge \text{ delta}\right) - \text{Background Buffer Conjuage Base}\right]}\right) \quad \text{Equation 3}$$

2. The method of claim 1, wherein the feedback control mechanism that the ratio of the one or more virus inactivating reagents to the sample is determined independently of, or without, is a pH feedback loop.

* * * * *